US007321673B2

(12) United States Patent
Watai et al.

(10) Patent No.: US 7,321,673 B2
(45) Date of Patent: Jan. 22, 2008

(54) ENDOSCOPE IMAGE FILING SYSTEM AND ENDOSCOPE IMAGE FILING METHOD

(75) Inventors: Makoto Watai, Northport, NY (US); Hiroyuki Shibata, Yokohama (JP)

(73) Assignee: Olympus Corporation, Tokyo (JP)

( * ) Notice: Subject to any disclaimer, the term of this patent is extended or adjusted under 35 U.S.C. 154(b) by 628 days.

(21) Appl. No.: 10/308,456

(22) Filed: Dec. 3, 2002

(65) Prior Publication Data

US 2003/0128400 A1 Jul. 10, 2003

(30) Foreign Application Priority Data

Dec. 3, 2001 (JP) ............................ 2001-369044

(51) Int. Cl.
*G06K 9/00* (2006.01)

(52) U.S. Cl. .......................................... 382/128; 705/2

(58) Field of Classification Search ................ 382/128; 705/1, 2, 3; 707/103

See application file for complete search history.

(56) References Cited

U.S. PATENT DOCUMENTS 5,319,543 A * 6/1994 Wilhelm ........................ 705/3
5,740,801 A 4/1998 Branson
6,260,021 B1 * 7/2001 Wong et al. ................... 705/2
6,785,410 B2 * 8/2004 Vining et al. ............... 382/128
6,788,997 B1 * 9/2004 Frederick .................... 700/236
2002/0161795 A1 * 10/2002 O'Rourke ................... 707/500
2002/0172498 A1 * 11/2002 Esenyan et al. .............. 386/69
2005/0135662 A1 * 6/2005 Vining et al. ............... 382/128
2005/0251021 A1 * 11/2005 Kaufman et al. ........... 600/407

FOREIGN PATENT DOCUMENTS

| | | |
|---|---|---|
| JP | 200-33072 | 2/2000 |
| JP | 2000-033072 | 2/2000 |
| JP | 2000-181816 | 6/2000 |
| JP | 2001-325368 | 11/2001 |
| WO | WO 00/08585 | 2/2000 |
| WO | WO 00/33231 | 6/2000 |

* cited by examiner

*Primary Examiner*—Matthew C. Bella
*Assistant Examiner*—Tom Y Lu
(74) *Attorney, Agent, or Firm*—Scully, Scott, Murphy & Presser, P.C.

(57) ABSTRACT

The endoscope image filing system is constituted of an endoscope apparatus for obtaining endoscope images and an image filing device which is connected to the endoscope apparatus and which is for recording desired endoscope images. The image filing device registers endoscope image data that is related with medical data on an endoscope examination (examination data), registers an examination report created by combining the medical data (examination data) with examined images generated from the endoscope image data, and is capable of building a database for registering distribution destination data for this examination report on a hard disk. The image filing device is then capable of outputting the created examination report to an external network, on the basis of the distribution destination data.

19 Claims, 16 Drawing Sheets

21
CPU
21a
VRAM
21d
RAM
21c
ROM
21b
MONITOR
22
1
IMAGE MEMORY
21l
A/D CONVERSION UNIT
21k
VIDEO CIRCUIT
21j
ENDOSCOPE APPARATUS
2
COMMUNICATION I/F
21i
KEYBOARD I/F
21h
KEYBOARD
23
3
MOUSE I/F
21g
MOUSE
24
SCSI I/F
21f
HARD DISK
21e
NETWORK I/F
21m
EXTERNAL NETWORK
26

Figure 6:
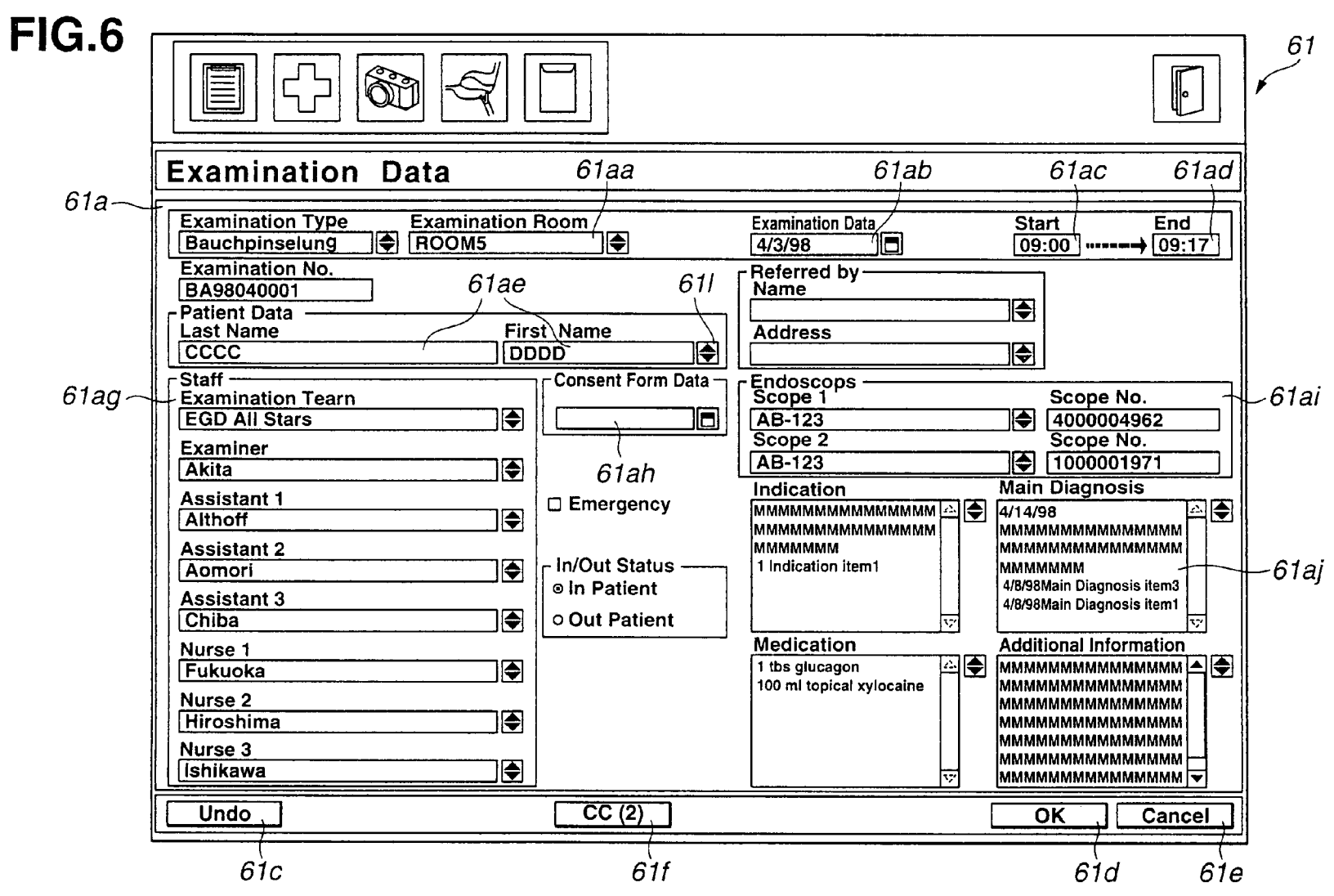

Examination Data

Examination Type
Bauchpinselung
Examination Room
ROOM5
Examination Data
4/3/98
Start
09:00
End
09:17
Examination No.
BA98040001
Patient Data
Last Name
CCCC
First Name
DDDD
Referred by
Name
Address
Staff
Examination Tearn
EGD All Stars
Examiner
Akita
Assistant 1
Althoff
Assistant 2
Aomori
Assistant 3
Chiba
Nurse 1
Fukuoka
Nurse 2
Hiroshima
Nurse 3
Ishikawa
Consent Form Data
Emergency
In/Out Status
In Patient
Out Patient
Endoscops
Scope 1
AB-123
Scope No.
4000004962
Scope 2
AB-123
Scope No.
1000001971
Indication
MMMMMMMMMMMMMMMMM
MMMMMMMMMMMMMMMMM
MMMMMMM
1 Indication item1
Main Diagnosis
4/14/98
MMMMMMMMMMMMMMMMM
MMMMMMMMMMMMMMMMM
MMMMMMM
4/8/98Main Diagnosis item3
4/8/98Main Diagnosis item1
Medication
1 tbs glucagon
100 ml topical xylocaine
Additional Information
MMMMMMMMMMMMMMMMM
MMMMMMMMMMMMMMMMM
MMMMMMMMMMMMMMMMM
MMMMMMMMMMMMMMMMM
MMMMMMMMMMMMMMMMM
MMMMMMMMMMMMMMMMM
Undo
CC (2)
OK
Cancel 61a 61aa 61ab 61ac 61ad 61ae 61l 61ag 61ah 61ai 61aj 61c 61f 61d 61e

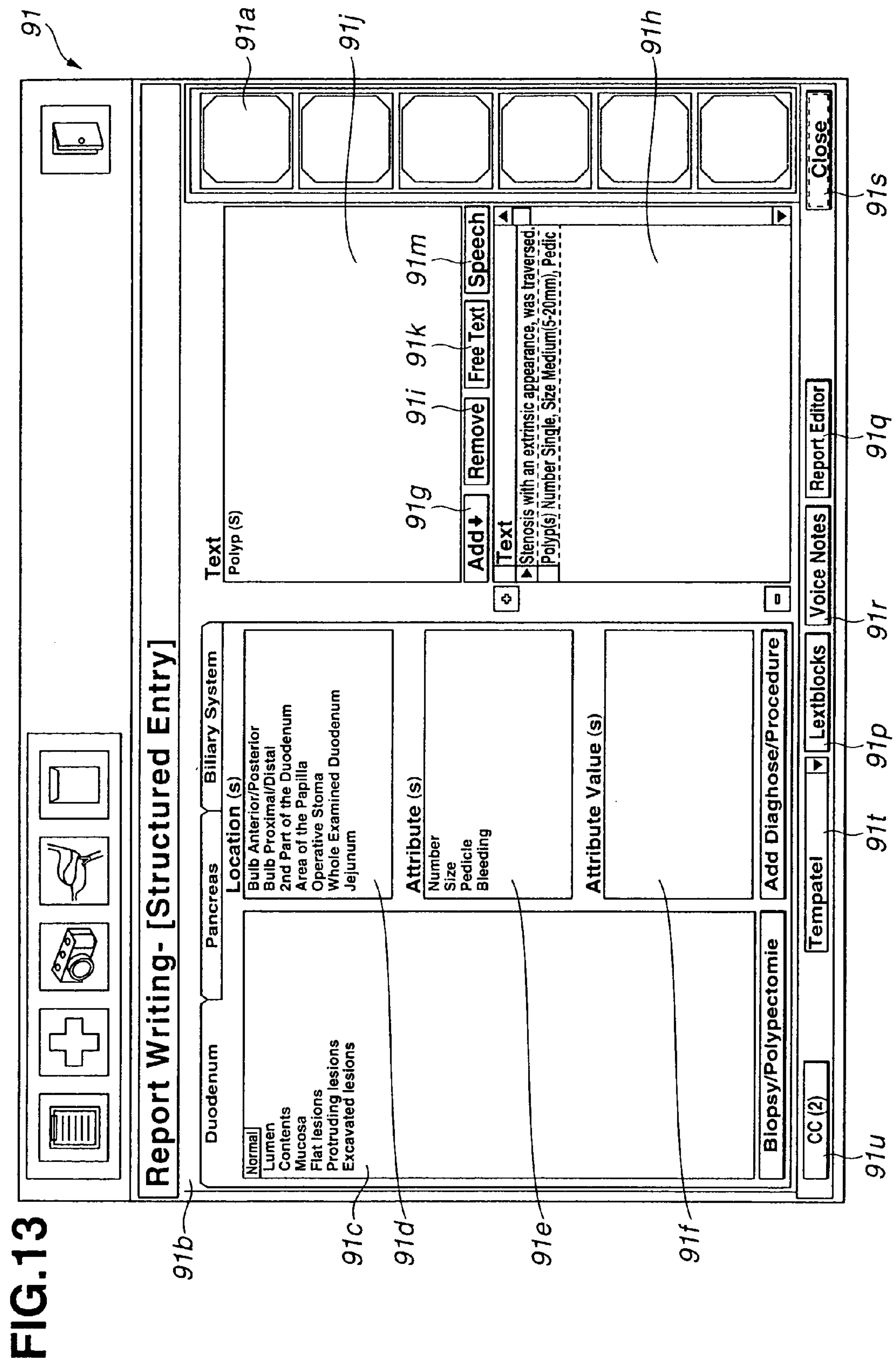
FIG.13
Report Writing- [Structured Entry]
Duodenum
Pancreas
Biliary System
Normal
Lumen
Contents
Mucosa
Flat lesions
Protruding lesions
Excavated lesions
Location (s)
Bulb Anterior/Posterior
Bulb Proximal/Distal
2nd Part of the Duodenum
Area of the Papilla
Operative Stoma
Whole Examined Duodenum
Jejunum
Attribute (s)
Number
Size
Pedicle
Bleeding
Attribute Value (s)
Biopsy/Polypectomie
Add Diaghose/Procedure
Text
Polyp (S)
Add
Remove
Free Text
Speech
Text
Stenosis with an extrinsic appearance, was traversed.
Polyp(s) Number Single, Size Medium(5-20mm), Pedic
CC (2)
Tempatel
Lextblocks
Voice Notes
Report Editor
Close
91
91a
91b
91c
91d
91e
91f
91g
91h
91i
91j
91k
91m
91p
91q
91r
91s
91t
91u

ENDOSCOPE IMAGE FILING SYSTEM AND ENDOSCOPE IMAGE FILING METHOD

This application claims benefit of Japanese Patent Application No. 2001-369044 filed in Japan on Dec. 3, 2001, the contents of which are incorporated by this reference.

BACKGROUND OF THE INVENTION

1. Field of the Invention

The present invention relates to an endoscope image filing system and endoscope image filing method for recording endoscope image data obtained by an endoscope image apparatus.

2. Description of the Related Art

At present, endoscope apparatuses are widely used in the field of medicine and in industrial fields. An endoscope apparatus comprises an endoscope. The endoscope is used to monitor a target site when a long and narrow insert portion thereof is inserted into an object to be examined such as a body cavity, a plant or a machine. The endoscope apparatus uses image pickup means to pick up endoscope images obtained using the endoscope and causes display means such as a monitor to display the endoscope images.

An endoscope apparatus of this kind makes it possible to constitute an endoscope image filing system by connecting an image filing device. The image filing device records endoscope images obtained by the endoscope apparatus.

Such an endoscope image filing system has been proposed in the form of a system that permits the recording of endoscope images displayed by a monitor to the image filing device when an endoscope switch, for example, a release switch, which is provided in the endoscope apparatus, is depressed, as disclosed by Japanese Patent Laid-Open Application Publication No. 2000-033072, for example.

The above endoscope image filing system is capable of recording a variety of data relating to endoscope examinations in addition to being able to record endoscope images. This variety of data relating to endoscope examinations is, for example, patient data such as a patient's name, age, and gender; endoscope examination reserved data such as the endoscope examination reservation date, reservation time and examination type; and examined data such as an opinion of a physician or the like with regard to recorded endoscope images, the date on which the endoscope examination was performed, and the examination time, and so forth. The above endoscope image filing system is also capable of extracting a variety of data related to the endoscope images and endoscope examinations and the like by means of a variety of retrieval means.

The endoscope image filing system is capable of creating and storing examination reports relating to endoscope examinations by using a variety of data relating to the endoscope images and endoscope examinations, and the like. The endoscope image filing system is capable of viewing and printing the examination reports.

However, the conventional endoscope image filing system described above requires a terminal that runs on a system in order to extract the recorded examination reports through retrieval by the retrieval means, and to view and print such reports.

Consequently, in a location outside the system such as a remote location where a terminal is not installed, an examination report recorded on the above conventional endoscope image filing system can be confirmed only by means of a printout. The above conventional endoscope image filing system has thus proved to be inconvenient in a location outside the system where a terminal that runs on the system is not installed.

SUMMARY OF THE INVENTION

It is an object of the present invention to provide an image filing system and endoscope image filing method which output recorded examination reports to locations outside the system to permit confirmation of examination reports even in a remote location.

It is a further object of the present invention to provide an image filing system and endoscope image filing method capable of automatically transmitting the content of an examination report to a designated distribution destination.

It is a further object of the present invention to provide an image filing system and endoscope image filing method that permit an examination report to be confirmed instantaneously even in a location outside the system such as a remote location where a terminal is not installed.

The endoscope image filing system according to the present invention comprises endoscope examined data inputting means for inputting endoscope examined data; endoscope examined data recording means for recording endoscope examined data inputted by the endoscope examined data inputting means; distribution destination data inputting means capable of designating and inputting a distribution destination outside the system as the distribution destination for an examination report on an endoscope examination; report distribution destination data recording means for recording report distribution destination data inputted by the distribution destination data inputting means; examined image recording means for recording endoscope image data obtained by an endoscope apparatus by relating such data with the endoscope examined data; examination report creating means for creating an examination report by reading out endoscope image data from the endoscope image recording means to generate an endoscope image and by combining the examined image and the endoscope examined data; and distribution destination designating/outputting means for outputting a report created by the examination report creating means by designating a distribution destination outside the system on the basis of the report distribution destination data recorded by the report distribution destination data recording means.

The endoscope image filing method according to the present invention comprises: an endoscope examined data inputting step of inputting endoscope examined data; an endoscope examined data recording step of recording endoscope examined data inputted in the endoscope examined data inputting step; a distribution destination data inputting step capable of designating and inputting a distribution destination outside the system as the distribution destination of an examination report on an endoscope examination; a report distribution destination data recording step of recording report distribution destination data inputted in the distribution destination data inputting step; an examined image recording step of recording endoscope image data obtained by an endoscope apparatus by relating such data with the endoscope examined data; an examination report creating step of creating an examination report by reading out endoscope image data from the endoscope image recording step to generate an endoscope image and by combining the examined image and the endoscope examined data; and a distribution destination designating/outputting step of outputting a report created in the examination report creating step by designating a distribution destination outside the system on the basis of the report distribution destination data recorded in the report distribution destination data recording step.

Other characteristics and advantages of the present invention will become sufficiently clear by way of the following description.

BRIEF DESCRIPTION OF THE DRAWINGS

FIG. 6 shows an example of a screen display of an examined data editing screen;

FIG. 13 shows an example of a screen display of an examination report creation screen;

DESCRIPTION OF THE PREFERRED EMBODIMENTS

The first embodiment of the present invention will be described hereinbelow with reference to the drawings.

Figure 1:
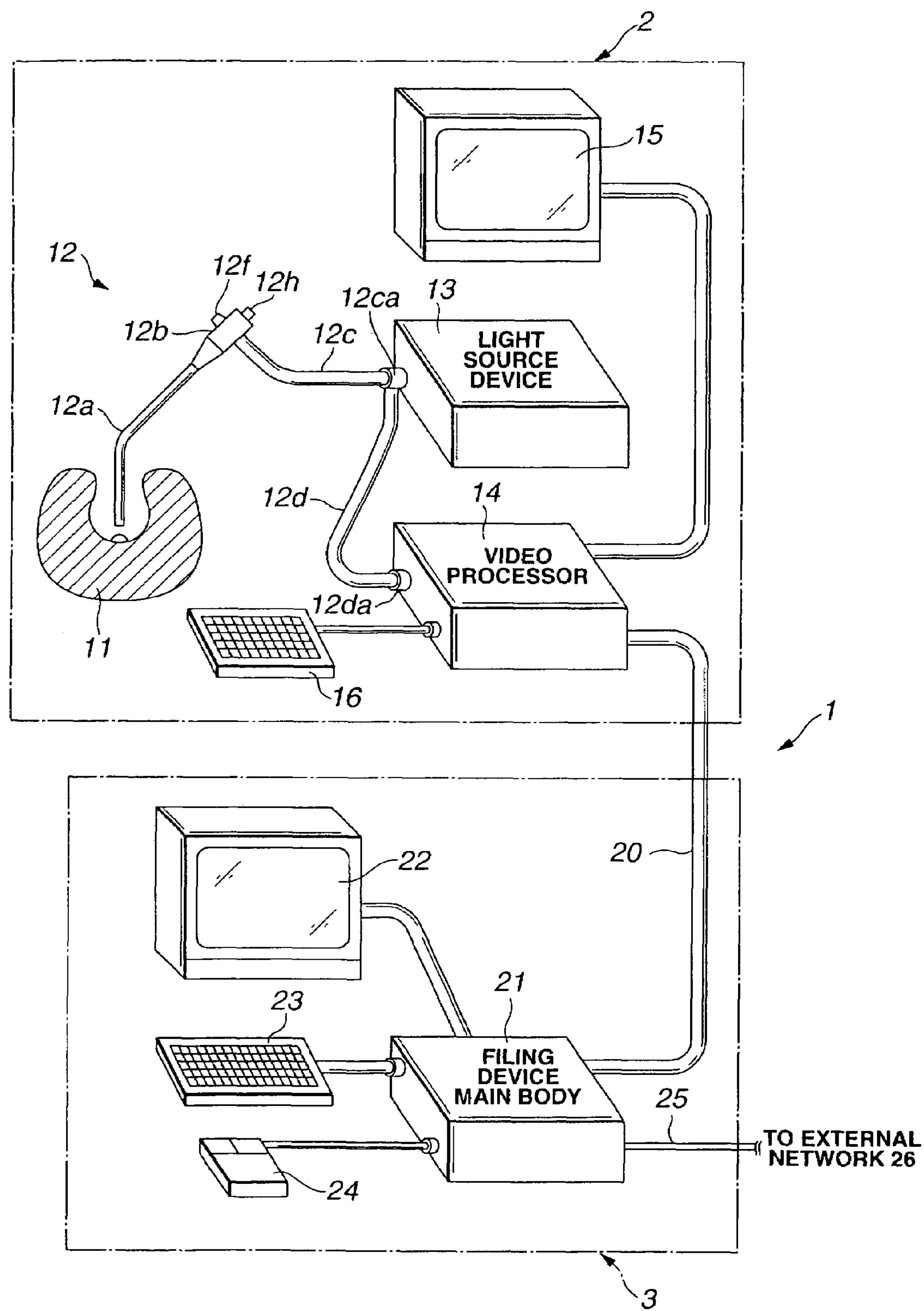
FIG. 1 is an overall constitutional view of the endoscope image filing system of the first embodiment of the present invention.

As shown in FIG. 1, the endoscope image filing system 1 according to the first embodiment of the present invention is principally constituted of an endoscope apparatus 2 for obtaining endoscope images and an image filing device 3 which is connected to the endoscope apparatus 2 and which is for recording desired endoscope images.

A description will be provided first for the constitution of the endoscope apparatus 2.

The endoscope apparatus 2 comprises an endoscope 12 which is inserted into a body cavity to pick up an image of a target site; a light source device 13 for supplying illuminating light to the endoscope 12; a video processor 14 for performing signal-processing an image pickup signal from the endoscope 12 to create an endoscope image; and a monitor 15 for displaying the endoscope image created by the video processor 14. The video processor 14 has a keyboard 16 for inputting data connected thereto.

The endoscope 12 is constituted having a long and narrow, flexible insert portion 12*a* which is inserted into a body cavity or similar, and an operation section 12*b* which is provided at the proximal end of the insert portion 12*a*. The endoscope 12 comprises a universal cable 12*c* which extends from the operation section 12*b*, and a connector 12*ca* at the end of this universal cable 12*c* is freely detachably connected to a light source device 13. Further, the endoscope 12 comprises an image pickup cable 12*d* which extends from the side of the connector 12*ca* of the universal cable 12*c*, and a connector 12*da* at the end of the image pickup cable 12*d* is detachably connected to the video processor 14.

A light guide (not shown), which propagates illuminating light, passes through the endoscope 12, and illuminating light, which is supplied from the light source device 13 via the universal cable 12*c*, is propagated to the tip of the insert portion 12*a* to illuminate a target site such as an affected area of a body cavity via an illumination window (not shown) at the tip of the insert portion 12*a*.

The endoscope 12 captures optical images of the target site thus illuminated, by means of an objective optical system (not shown) which is formed in the vicinity of the illumination window, and performs photoelectric conversion by means of an image pickup device (not shown) disposed at the focal position. The image pickup device outputs an image pickup signal obtained by this photoelectric conversion to the video processor 14 via a signal wire that passes through the universal cable 12*c* and the image pickup cable 12*d*. The endoscope 12 comprises, on the accessible side thereof, a freeze switch 12*f* for inputting an instruction to freeze an image, and a release switch 12*h* for inputting an instruction to record the image.

The light source device 13 is provided with a light source (not shown) which serves to generate the illuminating light. The light source device 13 is adapted to supply the illuminating light generated by the light source to the light guide of the endoscope 12.

The video processor 14 performs signal-processing for the image pickup signal inputted by the endoscope 12 to generate a standard RGB-type image signal. The video processor 14 outputs the generated image signal to a monitor 15, and causes the monitor 15 to display an endoscope image of the target site.

The video processor 14 also converts text data, which is inputted via a keyboard 16, to an image signal and superimposes this text data on the endoscope image. That is, the monitor 15 is able to display the text data such that same is synthesized with the endoscope image displayed on the display screen, whereby all kinds of messages can be relayed to the user of the endoscope apparatus 2.

The video processor 14 outputs the image signal not only to the monitor 15 but also to the image filing device 3. The video processor 14 is also capable of sending and receiving data to and from the image filing device 3, via a communication interface 20 of the commonly known RS-232C system, for example. The video processor 14 is also electrically connected to the release switch 4*h* of the endoscope 12 and is thus capable of detecting the operational states of the release switch 4*h*.

A description will be provided next for the image filing device 3.

The image filing device 3 comprises a filing device main body 21 as the principal part. A monitor 22 for displaying endoscope images and data, a keyboard 23 for inputting data, and a mouse 24 are connected to the filing device main body 21.

In the present embodiment, the filing device main body 21 of the image filing device 3 is connected to an external network via a network cable 25.

A description follows for the internal constitution of the filing device main body 21.

Figure 2:
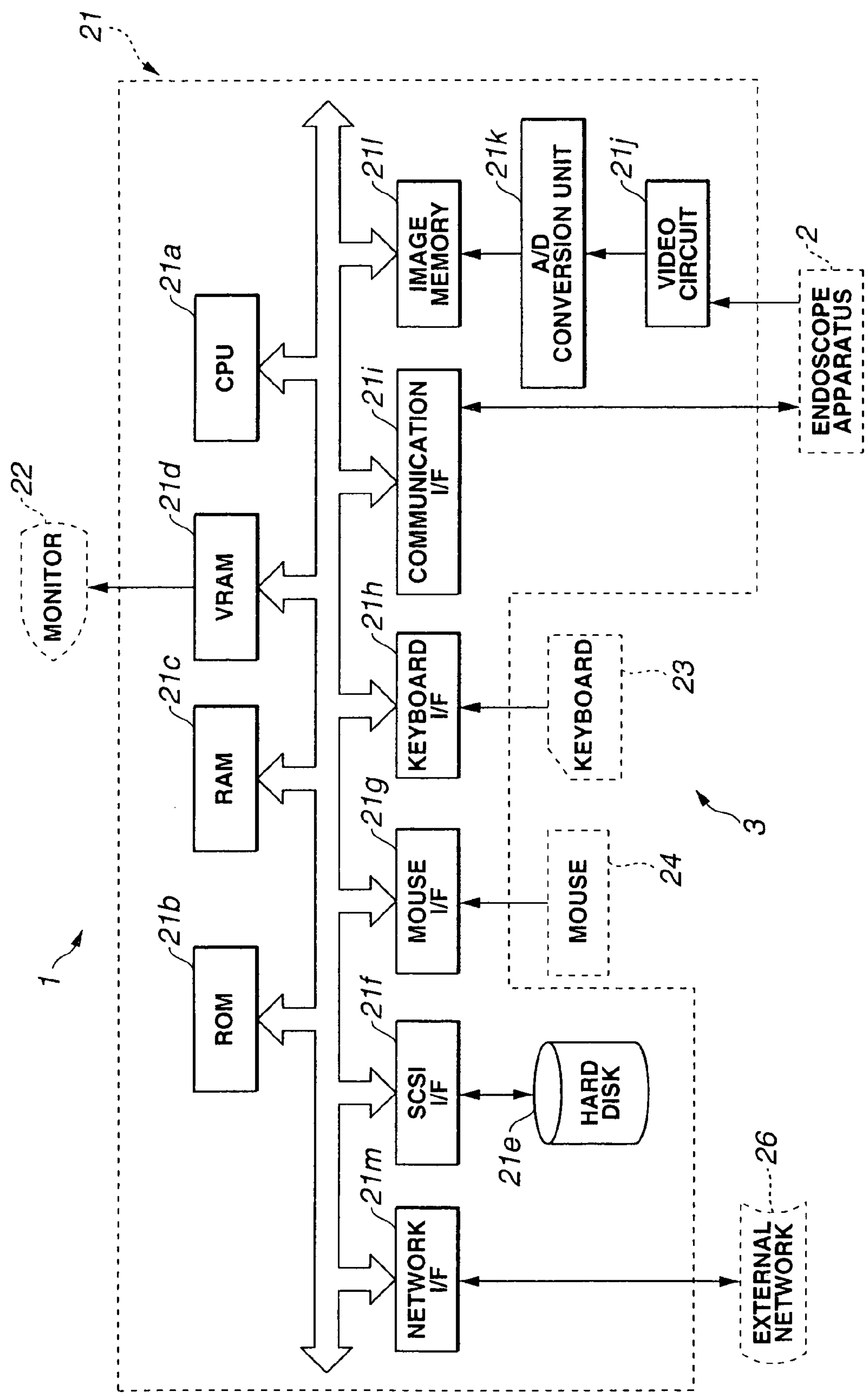
FIG. 2 is a block diagram illustrating the hardware constitution of the image filing device.

As shown in FIG. 2, the filing device main body 21 is constituted by a CPU 21*a*, which is the principal control means for controlling each component; a ROM 21*b* for storing programs that cause the CPU 21*a* to operate, and display messages for the monitor 22, or similar; a RAM 21*c*, which is used as the work region of the CPU 21*a* and as a buffer region for a variety of data; a VRAM 21*d* for buffering image data outputted to the monitor 22; a hard disk 21*e* for storing image data, and a variety of data; an SCSI interface (I/F) section 21*f* for sending and receiving data via the commonly known SCSI system to and from the hard disk 21*e*; a mouse I/F section 21*g* for detecting inputs via the mouse 24; a keyboard I/F section 21*h* for detecting inputs via the keyboard 23; a communication I/F section 21*i* of the commonly known RS232C system, for example, for sending and receiving a variety of data to and from the endoscope apparatus 2; a video circuit 21*j*, which is an I/F circuit for inputting image signals outputted by the endoscope apparatus 2; an A/D conversion section 21*k* for A/D converting an image signal inputted by the video circuit 21*j*; an image memory 211 for buffering image data outputted by the A/D conversion section 21*k*; and a network I/F 21*m* for sending and receiving a variety of data to and from an external network 26. The filing device main body 21 comprises a printer I/F (not illustrated) for connecting a printer (not shown) and is constituted so as to be capable of printing created examination reports, which will be described subsequently.

Here, the keyboard 23 and mouse 24 are endoscope examined data inputting means for inputting endoscope examined data, and are distribution destination data inputting means capable of designating and inputting a distribution destination outside the system which constitutes the distribution destination for an examination report on an endoscope examination.

The hard disk 21*e* is endoscope examined data recording means for recording endoscope examined data inputted by the endoscope examined data inputting means, and report distribution destination data recording means for recording report distribution destination data inputted by the distribution destination data inputting means. In addition, the hard disk 21*e* is endoscope image recording means for recording endoscope image data obtained by the endoscope apparatus by relating such data with the endoscope examined data. The hard disk 21*e* is also report distribution destination advance registration means for registering report distribution destination data in advance.

The CPU 21*a*, ROM 21*b*, and RAM 21*c* are: examination report creating means for creating an examination report by reading out endoscope image data from the endoscope image recording means to generate an endoscope image and by combining the examined image and the endoscope examined data; and distribution destination designating/outputting means for designating and outputting a report created by the examination report creating means to a distribution destination outside the system on the basis of the report distribution destination data recorded by the report distribution destination data recording means.

In addition, the keyboard 23 and the mouse 24 are report distribution selecting means for selecting at least one report distribution means from a plurality of report distribution means for distributing the examination report.

The keyboard 23 and the mouse 24 are also adapted to select one or more report distribution destination data recorded by the report distribution destination data recording means, from report distribution destination advance registration means.

The image filing device 3, whose principal part is the filing device main body 21, thus displays image data obtained by the endoscope apparatus 2 on the monitor 22, and is also capable of dividing up the processing by the CPU 21*a* after obtaining the states of the release switch 12*h* of the endoscope apparatus 2, being capable of recording images to the hard disk 21*e*, for example.

The image filing device 3 registers endoscope image data that is related with medical data on an endoscope examination (examined data), registers an examination report created by combining the medical data (examined data) with examined images generated from the endoscope image data, and is capable of building a database for registering distribution destination data for this examination report on the hard disk 21*e*. This database is also capable of relating and registering, in advance, text data such as set phrases for the creation of an examination report, which permits the smooth and straightforward creation of an examination report.

The image filing device 3 is capable of outputting a created examination report to the external network 26, on the basis of distribution destination data.

The image filing device 3 is constituted such that, in accordance with the various screens displayed by the monitor 22, the user inputs data and instructions, and the like, via the keyboard 23 and the mouse 24, and the CPU 21*a* controls each component to execute processing in accordance with the inputted data and instructions, and the like. That is, the image filing device 3 is adapted to execute various processing according to the flow of the screens that are displayed by the monitor 22.

An outline will be provided next for the configuration of the screens of the image filing device 3.

Figure 3:
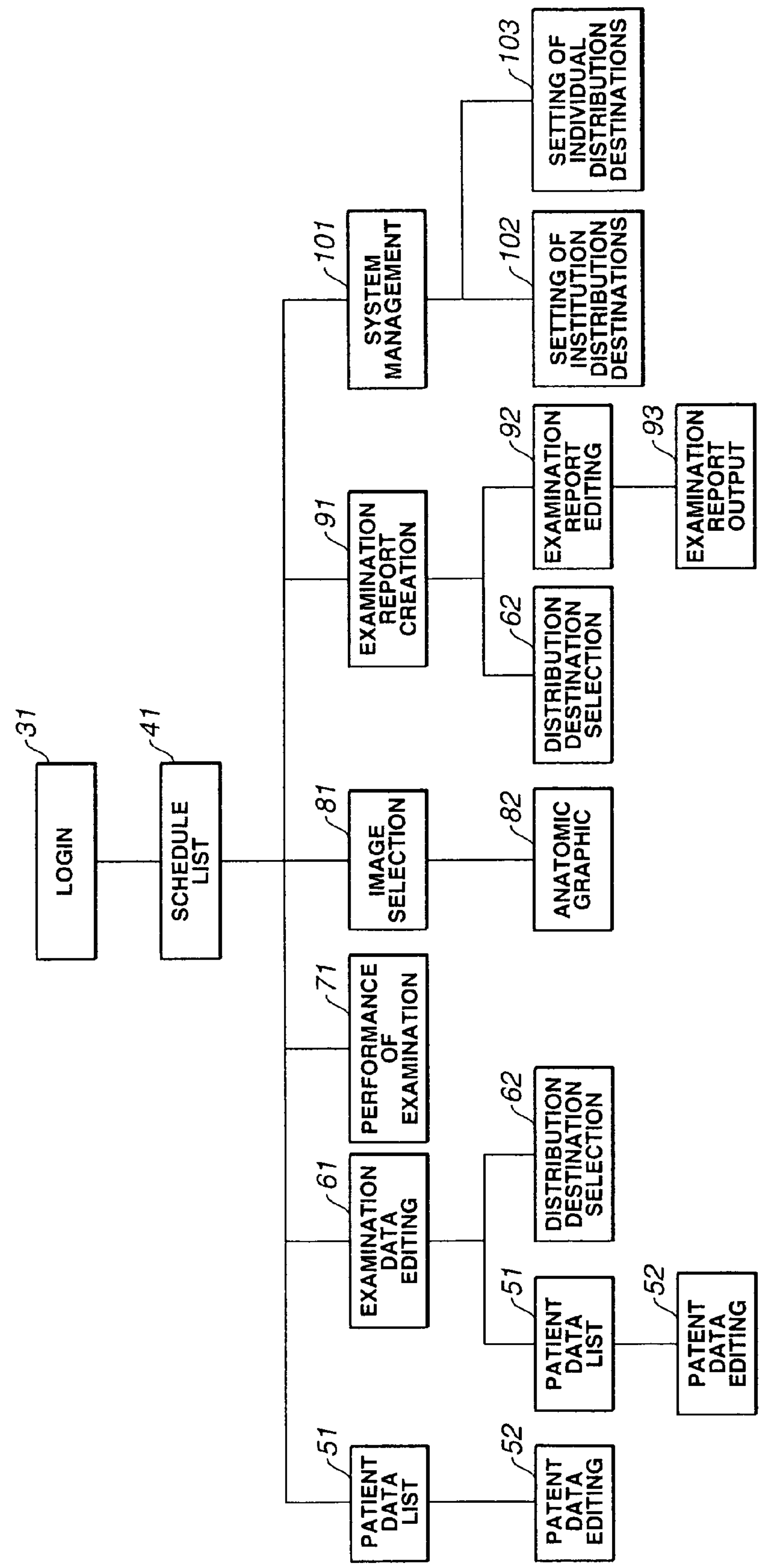
FIG. 3 is an explanatory view that provides an outline of the screen configuration of the image filing device.

As shown in FIG. 3, when the image filing device 3 first starts up, a login screen 31 for user authentication is displayed. When the user has been authenticated via the login screen 31, a schedule list screen 41, which displays a list of examination schedules, or similar, is displayed.

The schedule list screen 41 is capable of calling a patient list screen 51 that displays a patient data list. This patient list screen 51 makes it possible to newly register patient data and is capable of calling a patient data editing screen 52 for editing patient data which has already been registered.

The schedule list screen 41 also makes it possible to newly register examining data to make an examination reservation, and to call an examined data editing screen 61 for editing examined data that has already been registered. The schedule list screen 41 is also capable of calling an examination performance screen 71 which is for performing an examination upon connecting to the endoscope apparatus 2 and of capturing an image signal from the endoscope apparatus 2, and so forth. The schedule list screen 41 is also capable of calling an image selection screen 81 for selecting images in an examination report which is being created, from among captured images.

The schedule list screen 41 is capable of calling an examination report creation screen 91 which is a screen for creating examination reports. Further, the examination report creation screen 91 is capable of making a transition to an examination report editing screen 92 that has different functions. The examination report editing screen 92 is capable of calling an examination report output screen 93 for outputting an examination report.

Furthermore, the schedule list screen 41 is capable of calling a system management screen 101 for inputting a variety of system settings data. This system management screen 101 is capable of calling an institution distribution setting screen 102 for setting distribution data for an examination report for an institution. The system management screen 101 is also capable of calling an individual distribution destination setting screen 103 for setting distribution data for an examination report for an individual.

An example will be described next of the overall flow of the operation of the image filing device 3.

Figure 4:
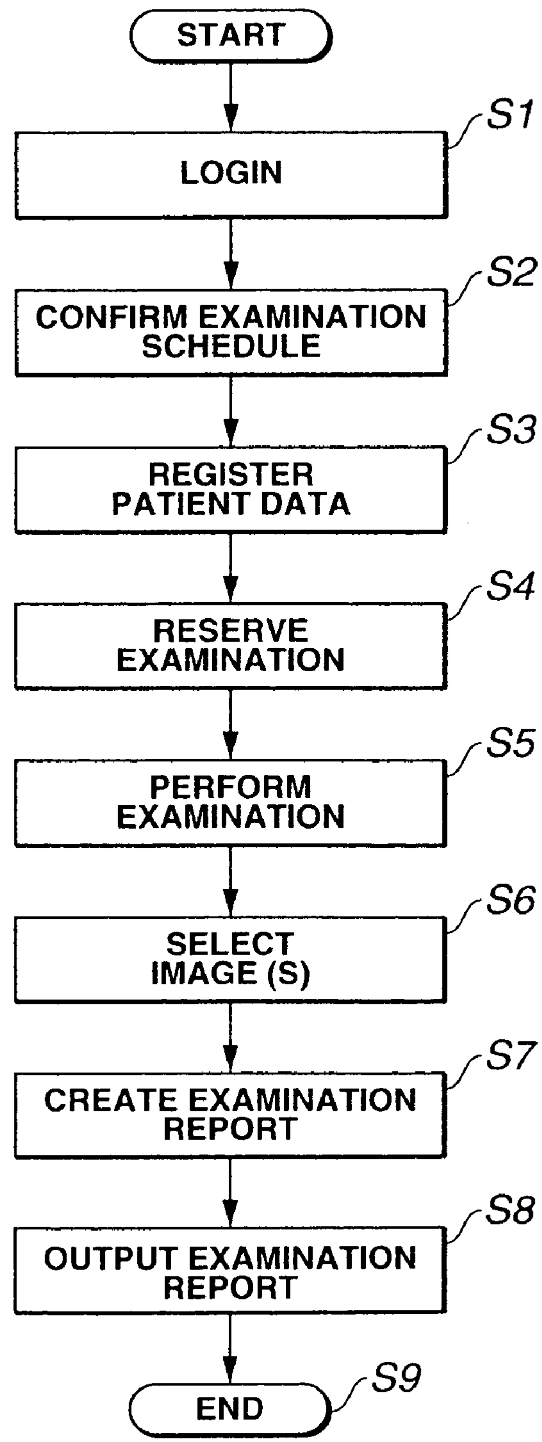
FIG. 4 is a flowchart providing an overall picture of the flow of the operation of the image filing device.

The reference numerals S1 to S8 in FIG. 4 are reference numerals assigned to processing steps. These processing steps are performed through control by the CPU 21*a* of the image filing device 3 on the basis of operation by the user.

First, the user starts up the image filing device 3. The CPU 21*a* of the image filing device 3 thus causes the display screen of the monitor 22 to display the login screen 31. The login screen 31 is for carrying out user authentication and so forth. When the user logs on following this authentication, the CPU 21*a* causes the display screen of the monitor 22 to display the schedule list screen 41 (step S1). The user then confirms an examination schedule via the schedule list screen 41 (step S2).

Next, when the patient to undergo an (endoscope) examination is a new patient, the user calls the patient list screen 14 and the patient data editing screen 15, and registers this patient data (step S3). Here, once the patient list screen 14 or the patient data editing screen 15 has been called, the CPU 21*a* causes the display screen of the monitor 22 to display this screen. Thereafter, although a description is omitted here, every time the user calls a display screen, the CPU 21*a* causes the called screen to be displayed on the display screen of the monitor 22.

The user then calls the examination report editing screen 61 and inputs a new examination reservation (step S4). Then the user calls the examination performance screen 71, performs an examination by means of the endoscope apparatus 2 connected to the image filing device 3, and stores endoscope images obtained by the endoscope apparatus 2 in the image filing device 3 (step S5).

The user then calls the image selection screen 81 and selects the endoscope images which are to be referenced in the examination report, from among the endoscope images obtained in the course of the examination (step S6).

Next, the user calls the examination report creation screen 91 to create an examination report (step S7) and calls the examination report editing screen 92 to edit the examination report.

The user then calls the examination report output screen 93 to confirm and output the output content (step S8), and ends the processing (step S9).

The above description is an example of the overall flow of the operation of the image filing device 3.

The constitution and operation of each screen will be described in detail below. Here, the examination data, endoscope images and examination report described below are related in a single examination and registered in the database of the hard disk 21*e*.

In the drawings to which reference is made in the present embodiment, English and German words are used for the display of messages and the like in the drawings that show the screen displays, but Japanese or another language and diagram may be used.

A description is provided first for the schedule list screen 41.

Figure 5:
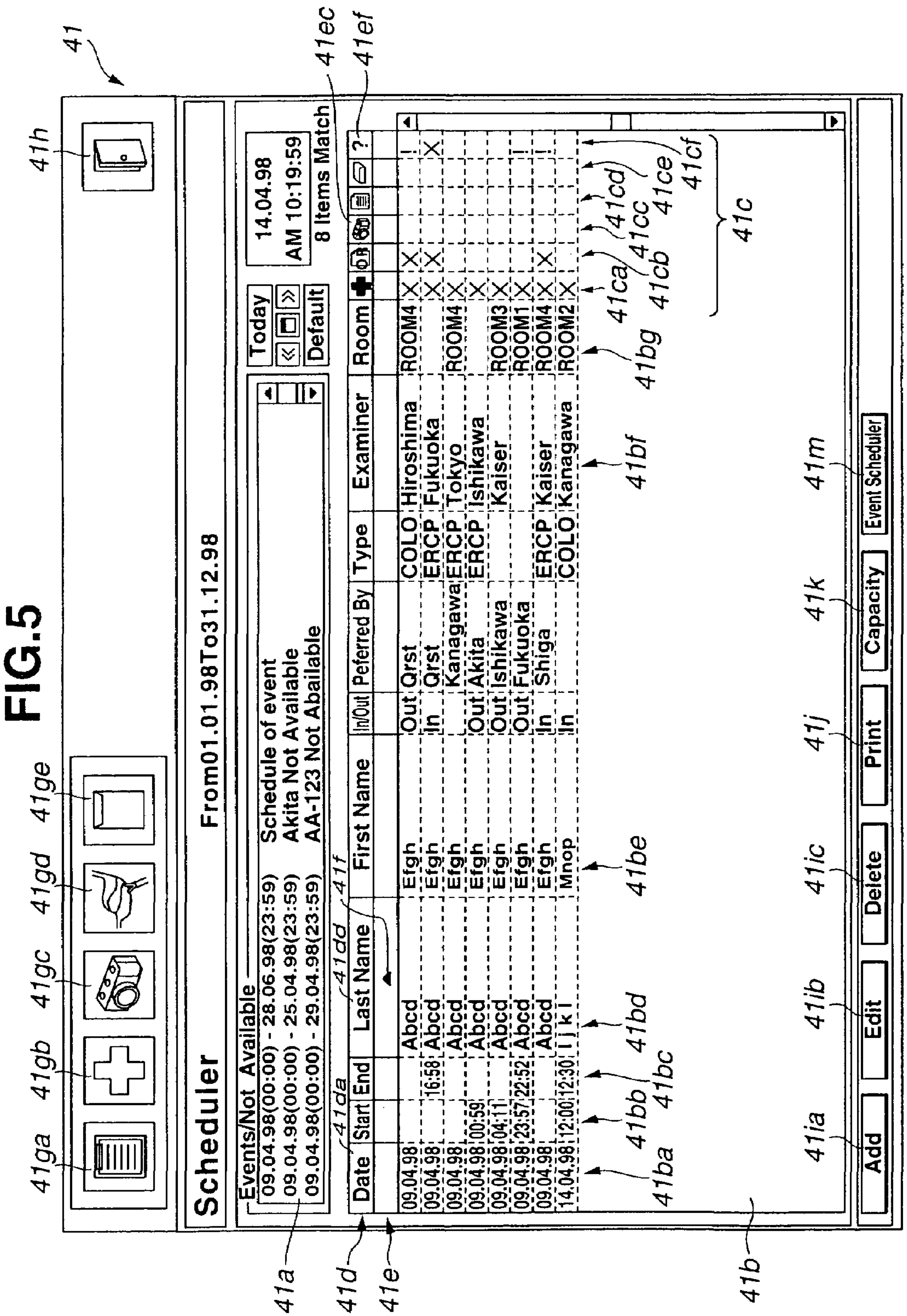
FIG. 5 shows an example of a screen display of a schedule list screen.

FIG. 5 shows an example of a screen display of the schedule list screen 41.

A resource schedule list display area 41*a*, which displays a list of schedules for examination resources, is disposed in the schedule list screen 41. In the present embodiment, the term “examination resource” indicates a physician, nurse or technician, or other responsible party, pertaining to the examination, the examination room used for the examination, and the materials used for the examination. Data contained in one resource schedule is known as a resource schedule record.

One resource schedule record is displayed as one line in the resource schedule list display area 41*a*. A resource schedule record displayed in one line in the resource schedule list display area 41*a* contains the resource usage start date and time, the usage end date and time, and the resource name, which is the title of the resource, and so forth.

Also disposed in the schedule list screen 41 is an examination data list display area 41*b* which displays a list of examination data. In the present embodiment, one item of examination data is known as an examination data record.

The first row of the examination data list display area 41*b* displays the heading for each data item constituting an examination data record. The examination data records are displayed from the third row of the examination data list display area 41*b*. One examination data record is displayed in one row of the examination data list display area 41*b*.

The data items constituting the examination data record include an examination date 41*ba*, an examination start time 41*bb*, an end time 41*bc*, a patient’s last name 41*bd*, a patient’s first name 41*be*, a person in charge of the examination 41*bf*, a name of an examination room used 41*bg*, and the like.

Examination state display fields 41*c*, which are for displaying states such as the respective state of progress of work relating to the examinations, are disposed in the examination data display area 41*b*.

Examination state display fields 41*ca* to 41*cf* are provided in the examination state display fields 41*c*. Wherein, an examination state where numerical letters are displayed in an examination state display field 41*c* indicates that images of a patient target site have already been obtained by means of an endoscope examination.

A classification, of whether all required input items of examination data and all required data input items for a patient who is to undergo the examination have been inputted, is displayed in an examination state display field 41*ca*. For example, when all such items have been inputted, the examination state display field 41*ca* displays the symbol “X”, otherwise the field is blank.

A classification, of whether the date on which an examination consent form is received from the patient has been inputted, is displayed in an examination state display field 41*cb*. For example, if already executed, the examination state display field 41*cb* has the number of images recorded in the examination displayed therein, and if not, this field is blank.

A classification, of whether an examination report has been created, is displayed in an examination state display field 41*cd*. For example, when such an examination report has been created, examination state display field 41*cd* has the symbol “X” displayed therein, and if not yet created, the field is blank.

The state of a biopsy examination result in a case, where a biopsy that involves taking a sample of biopsy tissue in an endoscope examination is carried out, is displayed in an examination state display field 41*cf*. For example, when a biopsy is performed and biopsy results have already been obtained, the examination state display field 41*cf* has the symbol "X" displayed therein and when a biopsy is performed and biopsy examination results have not yet been obtained, the symbol "!" is displayed in this field. When an examination has been performed but a biopsy has not been performed, the symbol "circle" is displayed, and when an endoscope examination has not yet been performed, the field is blank.

The examination data list display area 41*b* is not only capable of showing all of the examination data records but also capable of filtering the display to examination data records of interest only.

Disposed in the first row of the examination data list display area 41*b*, that is, in the positions of data items in a row in which item names or similar for the data items are displayed, are filter buttons 41*d* (41*da* or 41*dd*, or similar), which are buttons for calling respective screens to set filtering conditions for the data items.

The filter buttons 41*d* are buttons that are in a raised state when filtering conditions for the corresponding data items have not been set. Buttons in a raised state are on-screen buttons which are shown shaded such that same appear to have risen and buttons in a sunken state are on-screen buttons which are shown shaded such that same appear to have sunk.

Clicking on a raised filter button 41*d* displays a filtering conditions setting screen (not illustrated) for setting filtering conditions for the corresponding data items, whereby it is possible to input filtering conditions. Here, the inputting of filtering conditions in the filtering conditions setting screen causes the examination data list display area 41*b* to display only those examination data records which satisfy the filtering conditions.

On the other hand, the filter button 41*d* is in a sunken state in cases where filtering conditions have been set for the corresponding data items. When there are a plurality of filter buttons 41*d* in a sunken state, examination data records in the examination data list display area 41*b* are filtered and displayed according to an AND of the filtering conditions which are set by the filter buttons 41*d*. Clicking on a sunken filter button 41*d* cancels filtering conditions which have been set for the corresponding data item and the filter button 4 id becomes a raised button. For example, a filter button 41*ec* is a filter button corresponding to an examination state display field 41*cc* indicating whether an examination has been performed, and a filter button 41*ef* is a filter button corresponding to an examination state display field 41*cf* showing a classification for the state of a biopsy examination result.

Further, disposed at the top of the schedule list screen 41 are: a button 41*ga* for calling the patient list screen 51; a button 41*gb* for calling the examination data editing screen 61; a button 41*gc* for calling the examination performance screen 71; a button 41*gd* for calling the image selection screen 81; and a button 41*ge* for calling the examination report creation screen 91.

In addition, disposed in the top right-hand corner of the schedule list screen 41 is an Exit button 41*h* for ending the operation of the image filing device 3.

Further, disposed at the bottom of the schedule list screen 41 are: an Add button 41*ia* for calling the examination data editing screen 61 at the time of newly reserving an examination; an Edit button 41*ib* for selecting an examination data record in the examination data list display area 41*b* at the time of editing an examination data record already registered and for calling the examination data editing screen 61; a Delete button 41*ic* for selecting and deleting an examination data record in the examination data list display area 41*b*; a Print button 41*j* for printing a list of examination data; a button 41*k* for displaying the capacity status of an examination room; a button 41*m* for newly registering or editing data; and a button 41*n* for calling the system management screen 101. When these buttons are clicked, the corresponding processing is executed.

A description will be provided next for the examination data editing screen 61.

When the user clicks on the button 41*gb* of the schedule list screen 41, the examination data editing screen 61 is called.

FIG. 6 shows an example of a screen display of the examination data editing screen 61.

The examination data editing screen 61 as shown in FIG. 6 is a screen for newly registering or updating an examination data record.

The examination data editing screen 61 has a region 61*a* for the inputting of data items that are contained in an examination data record disposed therein. Disposed in the region 61*a* are, for example: a region 61*aa* for inputting the name of an examination room; a field 61*ab* for inputting an examination date; an input field 61*ac* for inputting an examination start time; an input field 61*ad* for inputting an examination end time; input fields 61*ae* for inputting the patient's last name and first name; an input field 61*ah* for inputting the date on which the examination consent form is received from the patient; a region 61*ai* comprising input fields for inputting the model numbers and the like of the endoscopes used for the examination; an input field 61*ag* for inputting the diagnosis result, and the like.

Disposed at the bottom of the examined data editing screen 61 are: an Undo button 61*c* which restores the state of the point at which the screen was displayed and permits the reediting of data in the region 61*a*; a Finish button 61*d* for newly registering or updating the examined data record and closing the examined data editing screen 61; a Cancel button 61*e* for closing the examined data editing screen 61 without newly registering or updating the examined data record; and a distribution destination setting button 61*f* for displaying a distribution destination setting screen 62. When the buttons 61*c* to 61*f* and the like are clicked, the corresponding processing is executed.

The distribution destination setting button 61*f* is constituted such that the number of distribution destinations set is displayed as a numerical letter in brackets in the button name display field.

A description will be provided next for the distribution destination setting screen 62.

When the user clicks on the distribution destination setting button 61*f* of the examination data editing screen 61, the distribution destination setting screen 62 is called.

Figure 7:
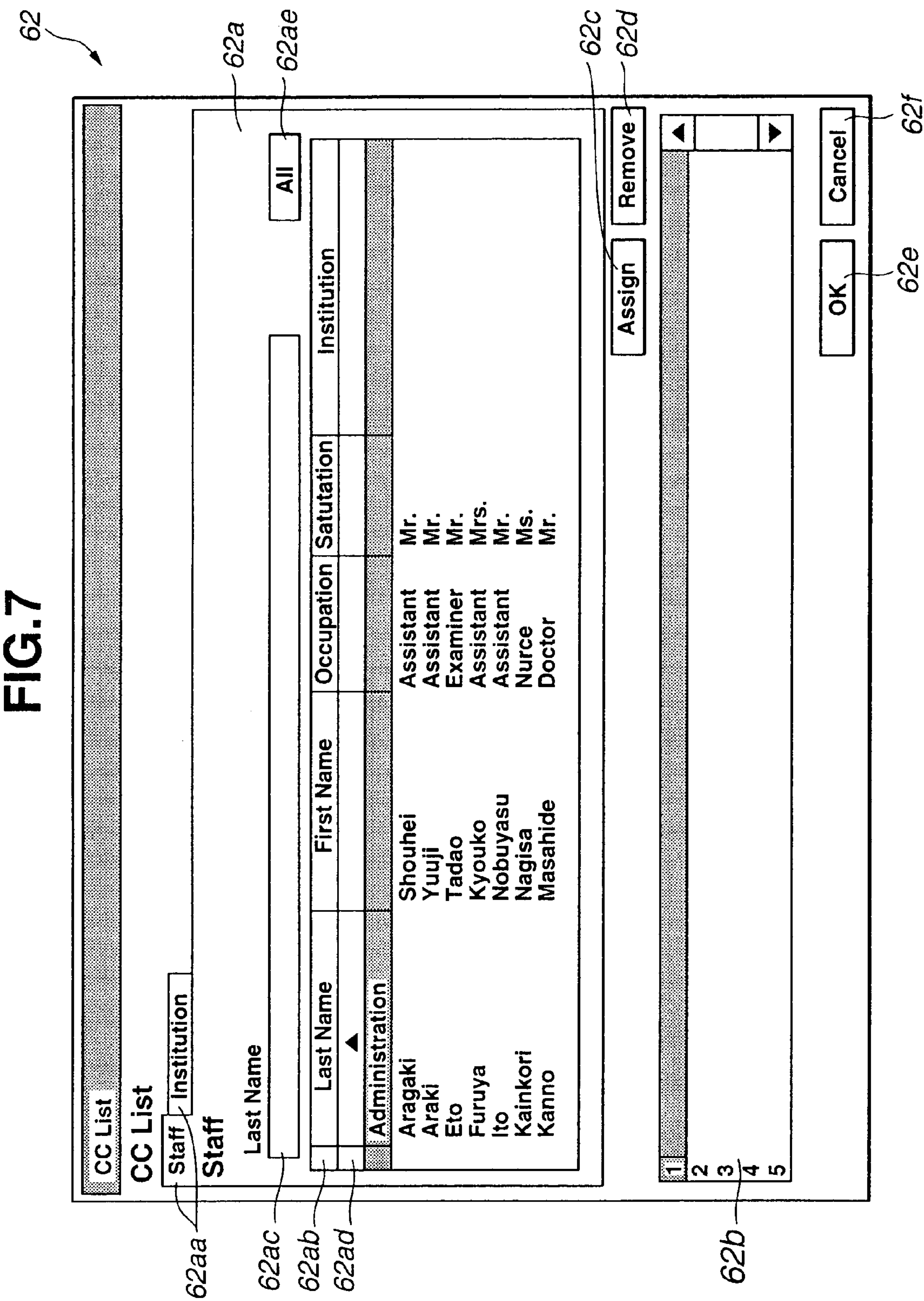
FIG. 7 shows an example of a screen display of a distribution destination setting screen.

FIG. 7 shows an example of a screen display of the distribution destination setting screen 62.

The distribution destination setting screen 62 as shown in FIG. 7 is a screen for setting distribution destinations at the time of outputting an examination report.

The distribution destination setting screen 62 has a distribution destination list 62*a* for selecting distribution destinations disposed therein.

Disposed at the top of the distribution destination list 62*a* are tabs 62*aa* for switching between an individual distribution destination list and an institution distribution destination list. Further, disposed in the distribution destination list 62*a* are: a search condition selection button 61*ab* for searching the distribution destination list, a search condition input region 62*ac*, which works with the search condition selection button 61*ab* and permits the inputting of search conditions; and a full list display button 62*ae* which, when clicked, displays all of the distribution destinations as a list.

Disposed in the distribution destination setting screen 62 is a selected distribution destination list display region 62*b* for displaying the selected distribution destinations as a list.

Disposed at the center of the distribution destination setting screen 62 are: a selection button 62*c* for registering the distribution destination data which is selected in the distribution destination list 62*a* as selected distribution destination data and displaying such data in the selected distribution destination list display region 62*b*; and a selection cancel button 62*d* for deleting selected distribution destination data selected in the selected distribution destination list display region 62*b*. When the buttons 62*c* and 62*d* are clicked, the corresponding processing is executed.

Further, selection of distribution destinations, in the same manner as using the selection button 62*c* is possible by double-clicking on items displayed in the distribution destination list 62*a*. The selection of distribution destinations can also be canceled, in the same manner as using the selection cancellation button, by double-clicking on items displayed in the selected distribution destination list display region 62*b*.

Disposed at the bottom of the distribution destination setting screen 62 are: a Finish button 62*e* for newly registering or updating report distribution destination data and closing the search data editing screen 62; and a Cancel button 62*f* for closing the distribution destination setting screen 62 without newly registering or updating report distribution destination data. When the buttons 62*e* and 62*f* are clicked, the corresponding processing is executed.

A description will be provided next for the examination performance screen 71.

When the user clicks on the button 41*gc* of the schedule list screen 41, the examination performance screen 71 is called.

Figure 8:
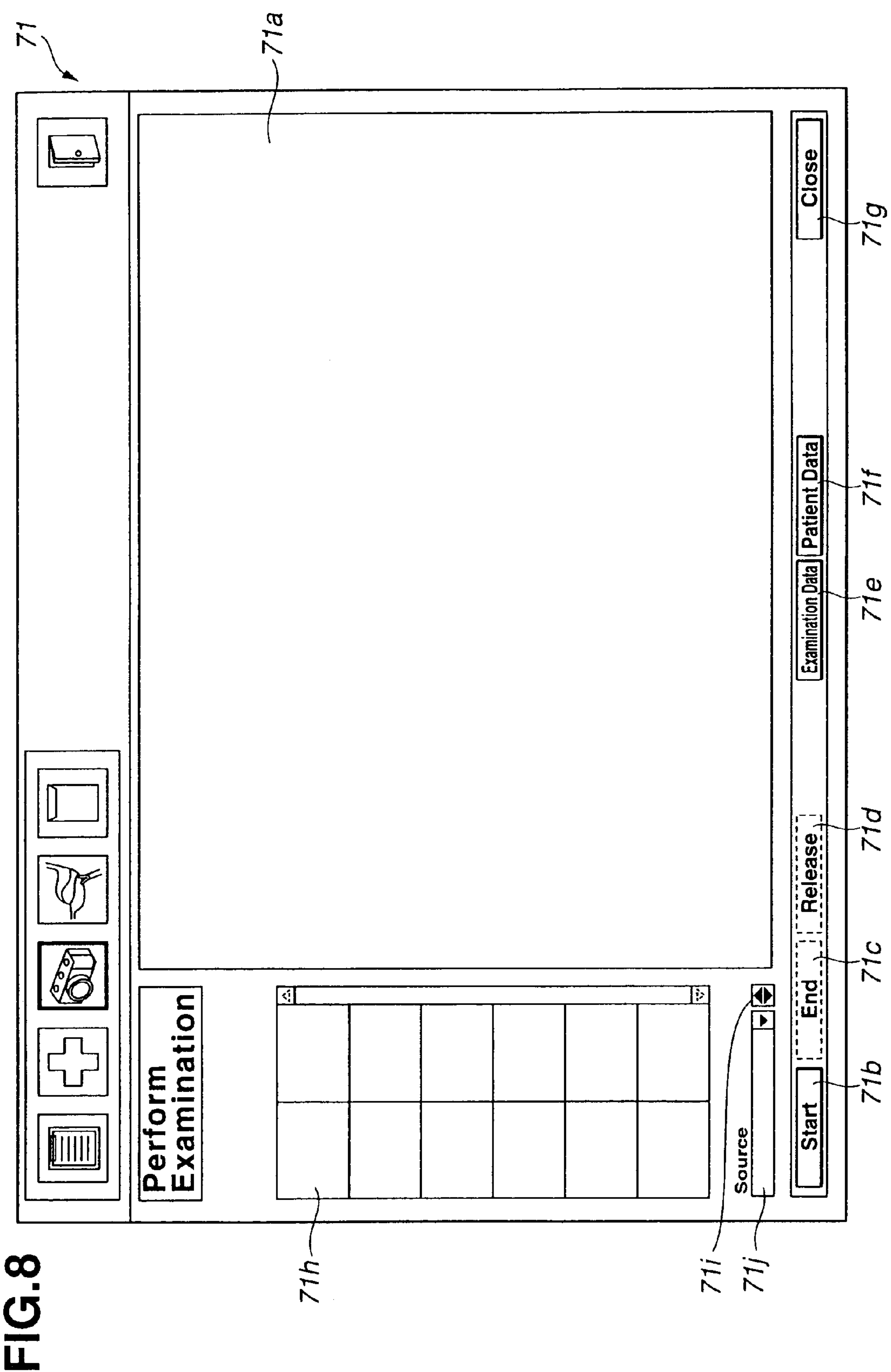
FIG. 8 shows an example of a screen display of an examination performance screen.

FIG. 8 is an example of a screen display of the examination performance screen 71.

The examination performance screen 71 as shown in FIG. 8 is a screen that operates on the image filing device 3 side, at the time of performing an examination using the endoscope apparatus 2.

Disposed in the examination performance screen 71 is an endoscope image display area 71*a* for displaying images picked up by the endoscope apparatus 2, that is, images that are the same as the images displayed by the monitor 15 of the endoscope apparatus 2.

At the bottom of the examination performance screen 71 are disposed: an examination start button 71*b* for relaying the start of the examination to the image filing device 3; an examination end button 71*c* for relaying the end of the examination to the image filing device 3; an image record button 71*d* for recording the image present when the button is clicked to the image filing device 3; and a Close button 71*g* for closing the examination performance screen 71, and so forth.

Disposed in the examination performance screen 71 is a thumbnail image display area 71*h* which displays thumbnail images of a plurality of images recorded by clicking on the image record button 71*d*, that is, images whose dimensions are reduced by a thin-out operation.

At the times when the examination start button 71*b* and the examination end button 71*c* are clicked, the respective images at the examination start time and the examination end time are recorded to the image filing device 3.

A description will be provided next for the image selection screen 81.

When the user clicks on the button 41*gd* of the schedule list screen 41, the image selection screen 81 is called.

Figure 9:
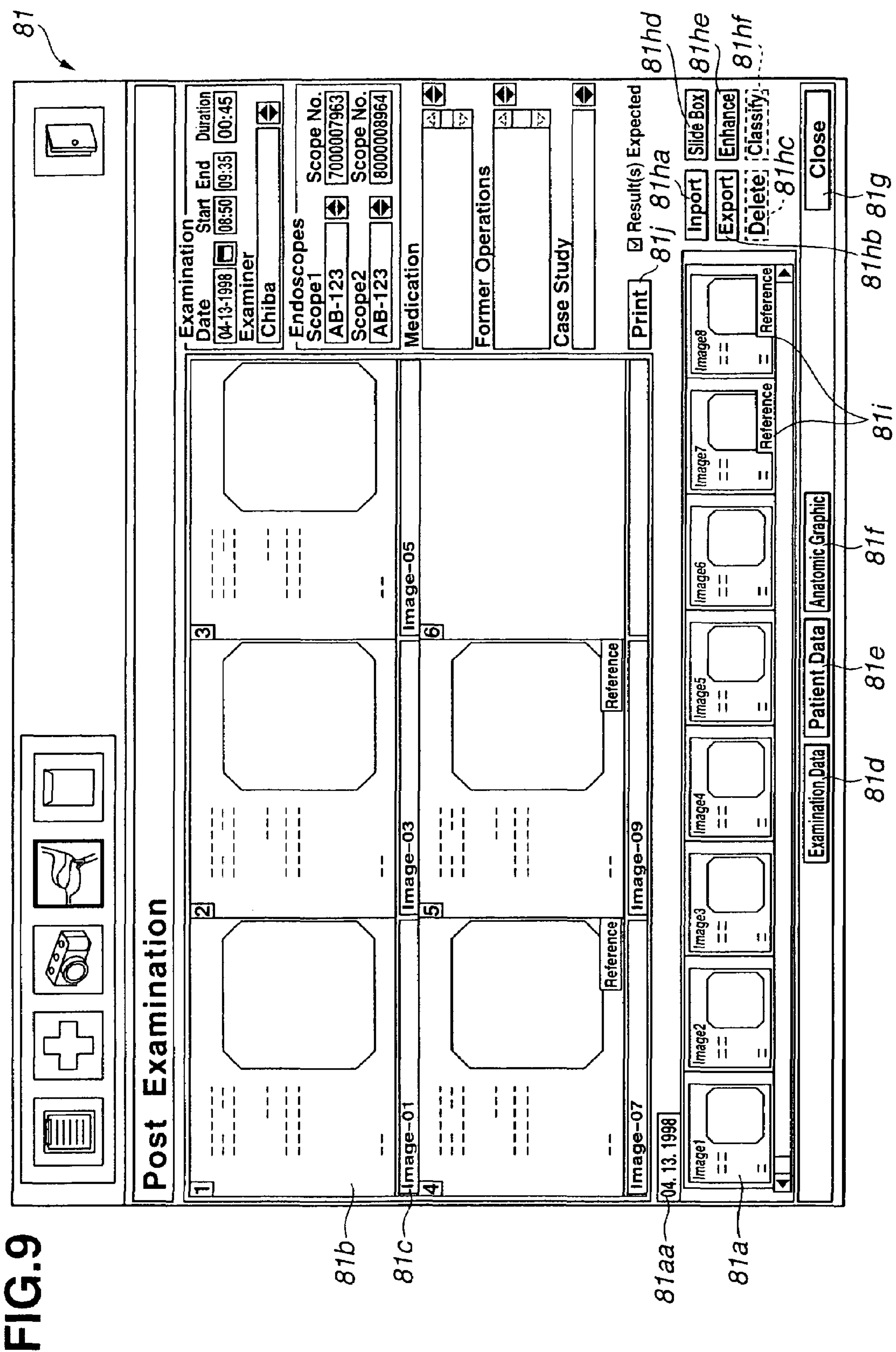
FIG. 9 shows an example of a screen display of an image selection screen.

FIG. 9 shows an example of a screen display of the image selection screen 81.

The image selection screen 81 as shown in FIG. 9 is a screen for carrying out post-examination processing that involves the selection of endoscope images to be referenced in an examination report from among endoscope images obtained in performing an examination, and so forth.

Disposed in the image selection screen 81 is a thumbnail display area 81*a* for displaying thumbnail images of all of the endoscope images obtained in the course of an examination.

When the mouse 24 is used to drag one thumbnail image of the thumbnail images displayed in the thumbnail image display area 81*a* and to drop this thumbnail image in a report image selection area 81*b*, the endoscope image that corresponds with this thumbnail image is displayed in the report image selection area 81*b*. The report image selection area 81*b* is an area for the selection of endoscope images to be referenced in an examination report.

Here, the term "drag" is intended to mean an operation in which the cursor of the mouse 24 is moved to an area of the screen and a state is maintained in which a push button provided on the mouse 24 is pressed without being released. Further, the term "drop" is intended to signify an operation where, after dragging using the mouse 24 and with the push button provided on the mouse 24 still pressed, the cursor of the mouse 24 is moved and the push button on the mouse 24 is released.

These drag and drop operations using the mouse 24 can be performed to allow endoscope images that are displayed in the thumbnail image display area 81*a* to be easily selected and displayed in the report image selection area 81*b*.

Also, by dragging one image among the images displayed in the report image selection area 81*b* and dropping this image outside the report image selection area 81*b*, the selection of the image thus dragged can be canceled.

Sometimes an endoscope examination is carried out a plurality of times rather than being performed once on an individual patient. The image selection screen 81 is constituted such that, in cases where images have been obtained in a plurality of examinations, the images obtained in examinations on the corresponding examination date are displayed in the thumbnail image display area 81*a*.

Furthermore, specifically, the image selection screen 81 displays and provides a plurality of examination date tabs 81*aa* at the top of the thumbnail image display area 81*a* that are buttons showing examination dates. Upon clicking on one of the plurality of examination date tabs 81*aa* that shows the date of the examination to be referenced, those images which were obtained in the examination on the corresponding examination date are displayed in the thumbnail image display area 81*a*. These thumbnail images can likewise be selected as images to be referenced in the examination report.

Figure 10:
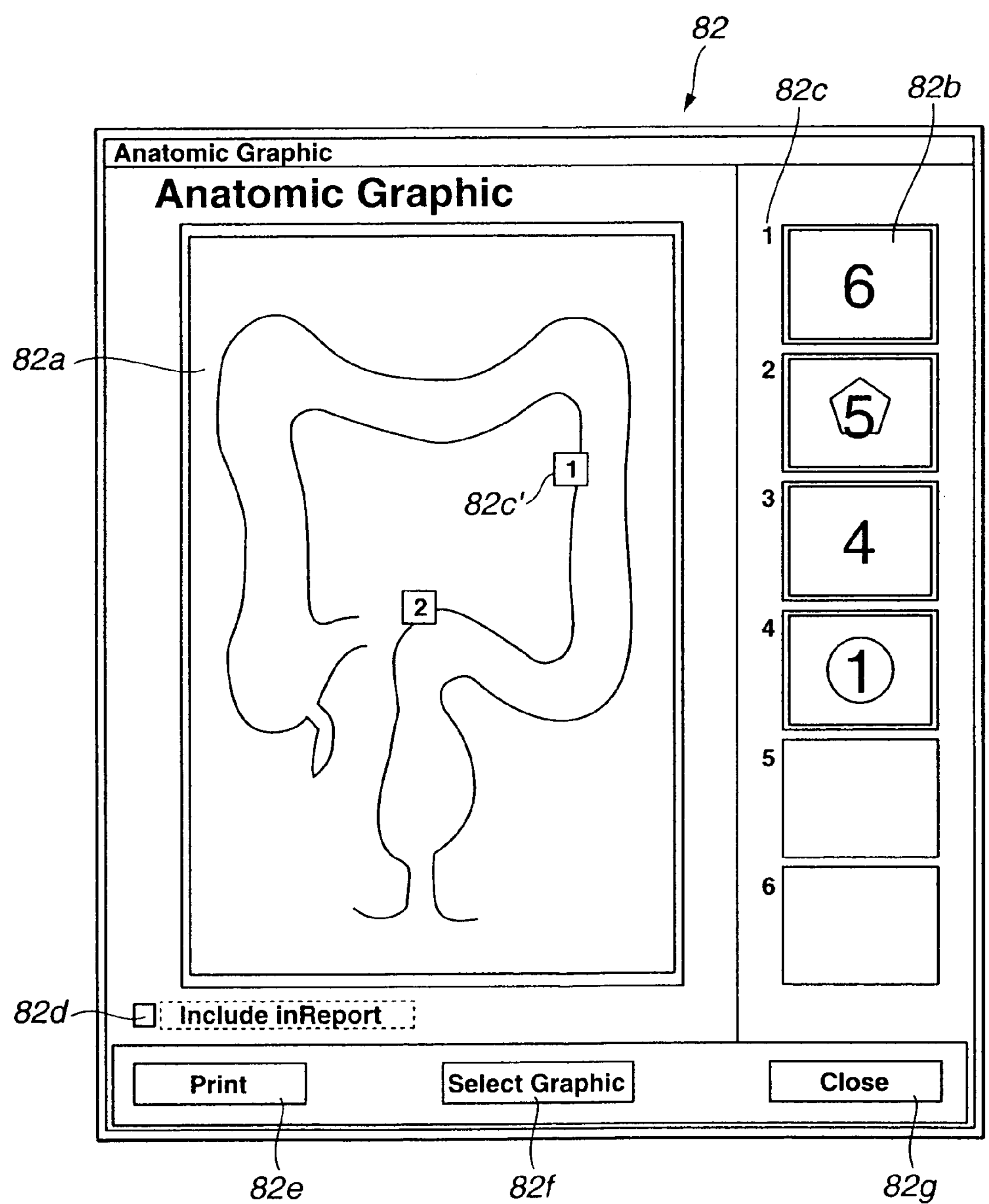
FIG. 10 shows an example of a screen display of an anatomic graphic screen.

Disposed at the bottom of the image selection screen 81 are: a button 81*f* for calling the anatomic graphic screen 82 shown in FIG. 10 and a button 81*g* for closing the image selection screen 81. When the buttons 81*f* and 81*g*, and the like, are clicked, the corresponding processing is executed.

A description will be provided next for the anatomic graphic screen 82.

When the user clicks on the button 81*f* of the image selection screen 81, an anatomic graphic screen 82 is called.

FIG. 10 shows an example of a screen display of the anatomic graphic screen 82.

The anatomic graphic screen 82 as shown in FIG. 10 is provided with an anatomic graphic display area 82*a* which displays a schematic diagram of a body part. In this example, a schematic diagram of a lower gastrointestinal tract is shown in the anatomic graphic display area 82*a*.

Disposed on the right-hand side of the anatomic graphic screen 82 is an image display area 82*b* which displays a plurality of images, for example six images, that have been selected from the thumbnail image display area 81*a* of the image selection screen 81 and transferred to the report image selection area 81*b*.

The images in the image display area 82*b* are displayed with the numbers 82*c* "[1]", "[2]", . . . , "[6]" arranged in order starting from the top of the screen, for example.

When one image of the plurality of images displayed in the image display area 82*b* is dragged and dropped in the anatomic graphic display area 82*a*, a number 82*c* that is the same as the number 82*c* corresponding to the dragged image is displayed at the point where the image is dropped.

Accordingly, each of the images displayed in the image display area 82*b* can be associated with an image at a particular location of the schematic diagram displayed in the anatomic graphic display area 82*a*.

When a button 82*d* is clicked, the graphic displayed in the anatomic graphic display area 82*a* is filed in the examination report.

Furthermore, disposed at the bottom of the anatomic graphic screen 82 are: a Print button 82*e* for printing the graphic which is displayed in the anatomic graphic display area 82*a*; a button 82*f* for calling a screen (not shown) for selecting the body schematic diagram displayed in the anatomic graphic display area 82*a*; and a Close button 82*g* for closing the anatomic graphic screen 82. When these buttons 82*e* to 82*g* are clicked, the corresponding processing is executed.

A description will be provided next for the institution distribution destination setting screen 102 and the individual distribution destination setting screen 103. The institution distribution destination setting screen 102 will be described first.

When the user clicks on the button 41*n* of the schedule list screen 41, the system management screen 101 is called. Then clicking on a call button (not shown) in the system management screen 101 calls the institution distribution destination setting screen 102.

Figure 11:
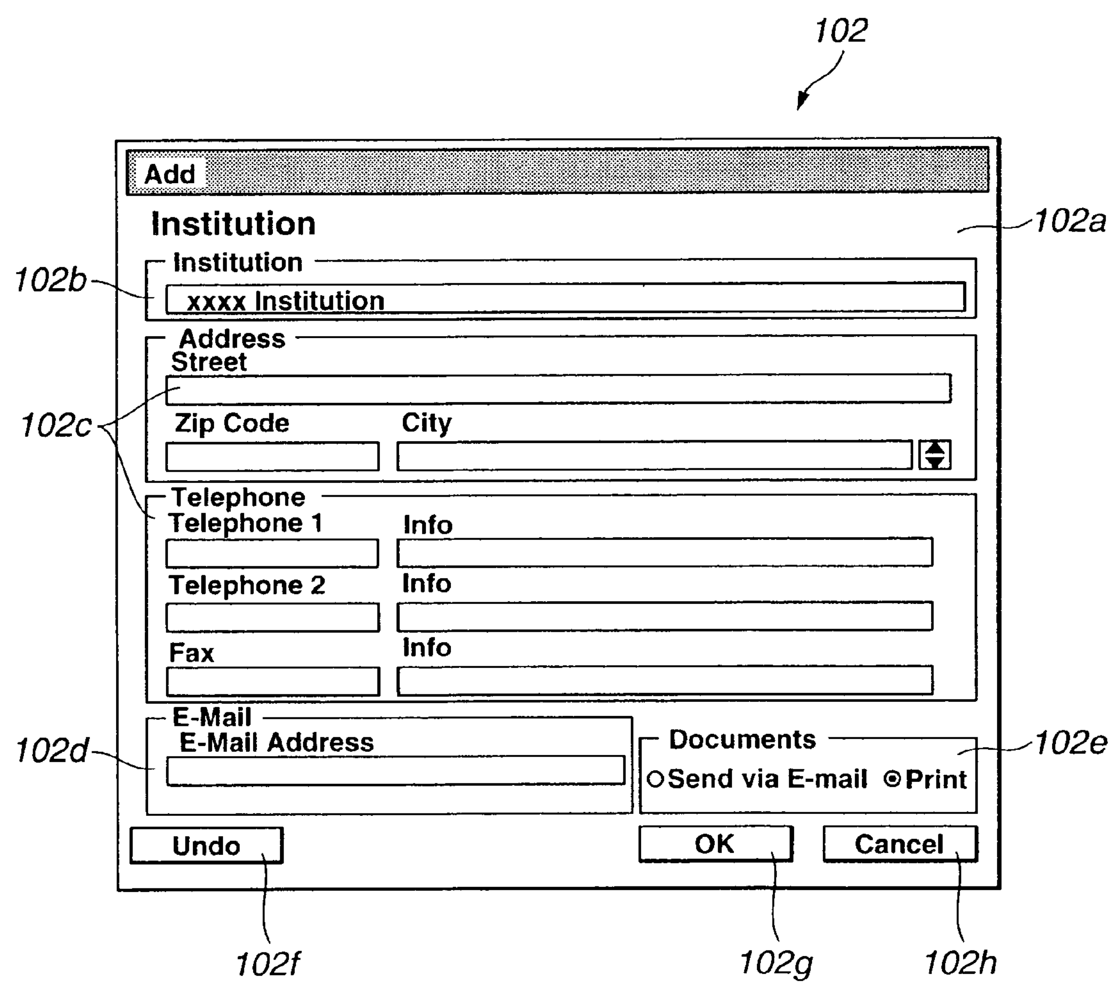
FIG. 11 shows an example of a screen display of an institution distribution destination setting screen.

FIG. 11 is an example of a screen display of the institution distribution destination setting screen 102.

The institution distribution destination setting screen 102 as shown in FIG. 11 is a screen for inputting institution distribution destination data for a newly registered examination report and for editing the details of existing institution distribution destination data.

A region 102*a* is a section for editing the details of institution distribution destination data. The region 102*a* comprises, for example: a region 102*b* for editing an identifier for the institution name or similar; regions 102*c* for editing the institution's address, the institution's zip code, the institution's telephone number, and the institution's fax number; a region 102*d* for editing the institution's electronic mail address; and a region 102*e* for editing the initial settings for the examination report distribution destination method.

Disposed at the bottom of the institution distribution destination setting screen 102 are: an Undo button 102*f* which restores the state of the point at which the screen was displayed and permits reediting; a Finish button 102*g* for newly adding or updating institution distribution destination data, closing the institution distribution destination setting screen 102, and returning to the system management screen 101; and a Cancel button 102*h* for closing the institution distribution destination setting screen 102 and returning to the system management screen 101 without newly adding or updating institution distribution destination data. When the buttons 102*f* to 102*h*, and the like, are clicked, the corresponding processing is executed.

A description will be provided next for the individual distribution destination setting screen 103.

When the user clicks a call button (not shown) of the system management screen 101, the individual distribution destination setting screen 103 is called.

Figure 12:
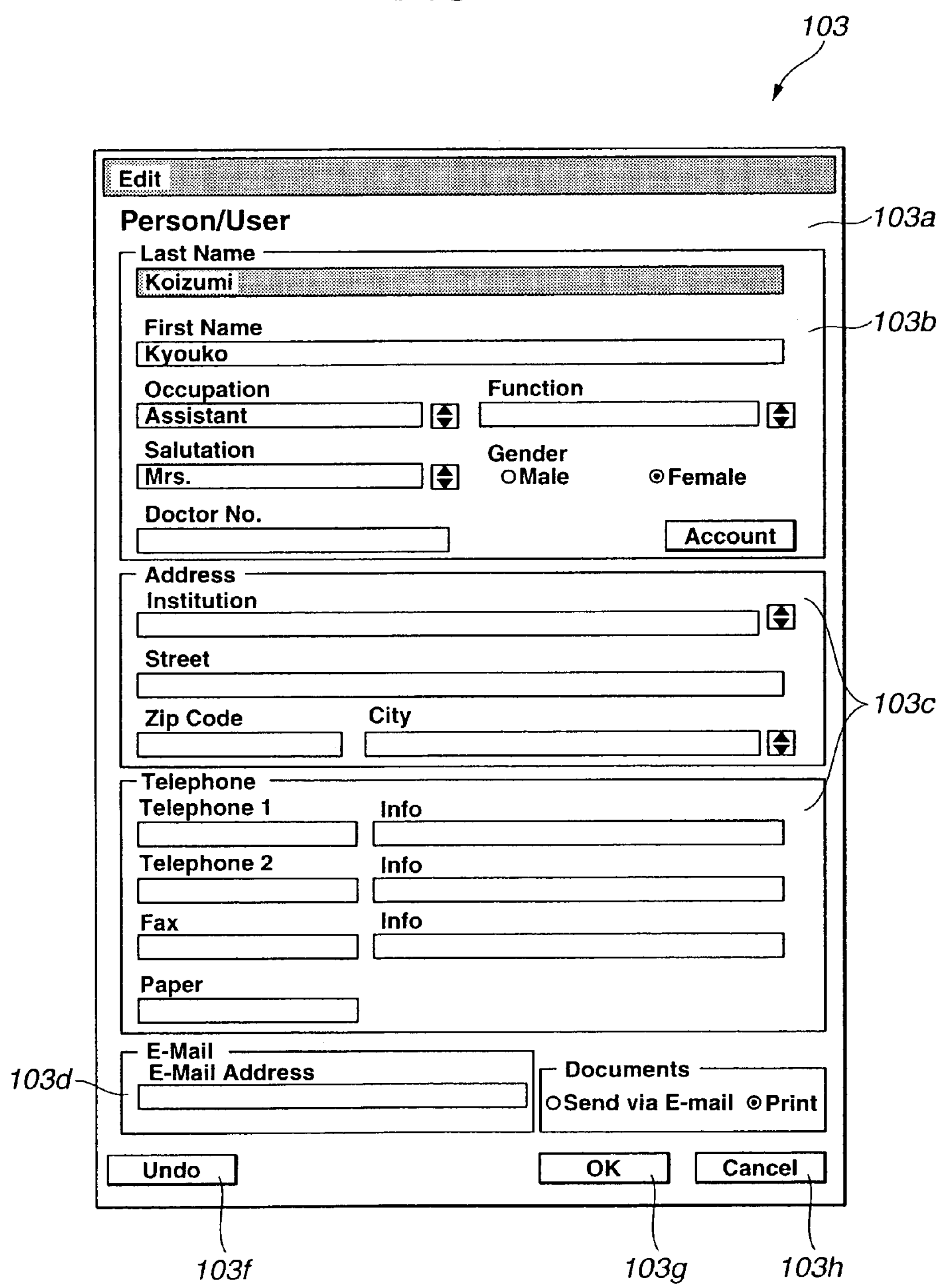
FIG. 12 shows an example of a screen display of an individual distribution destination setting screen.

FIG. 12 is an example of a screen display of the individual distribution destination setting screen 103.

The individual distribution destination setting screen 103 as shown in FIG. 12 is a screen for inputting individual distribution destination data for a newly registered examination report and for editing the details of existing individual distribution destination data.

A region 103*a* is a section for editing the details of individual distribution destination data. The region 103*a* comprises, for example: a region 103*b* for editing an identifier for the individual's name or similar; regions 103*c* for editing the address of an institution to which the individual belongs, the institution's zip code, the institution's telephone number, and the institution's fax number; a region 103*d* for editing the individual's electronic mail address; and a region 103*e* for editing the initial settings for the examination report distribution destination method.

Disposed at the bottom of the individual distribution destination setting screen 103 are: an Undo button 103*f* which restores the state of the point at which the screen was displayed and permits reediting; a Finish button 103*g* for newly adding or updating individual distribution destination data, closing the individual distribution destination setting screen 103, and returning to the system management screen 101; and a Cancel button 103*h* for closing the individual distribution destination setting screen 103 and returning to the system management screen 101 without newly adding or updating individual distribution destination data. When the buttons 103*f* to 103*h*, and the like, are clicked, the corresponding processing is executed.

Descriptions will be provided next for the examination report creation screen 91 and the examination report editing screen 92.

Figure 14:
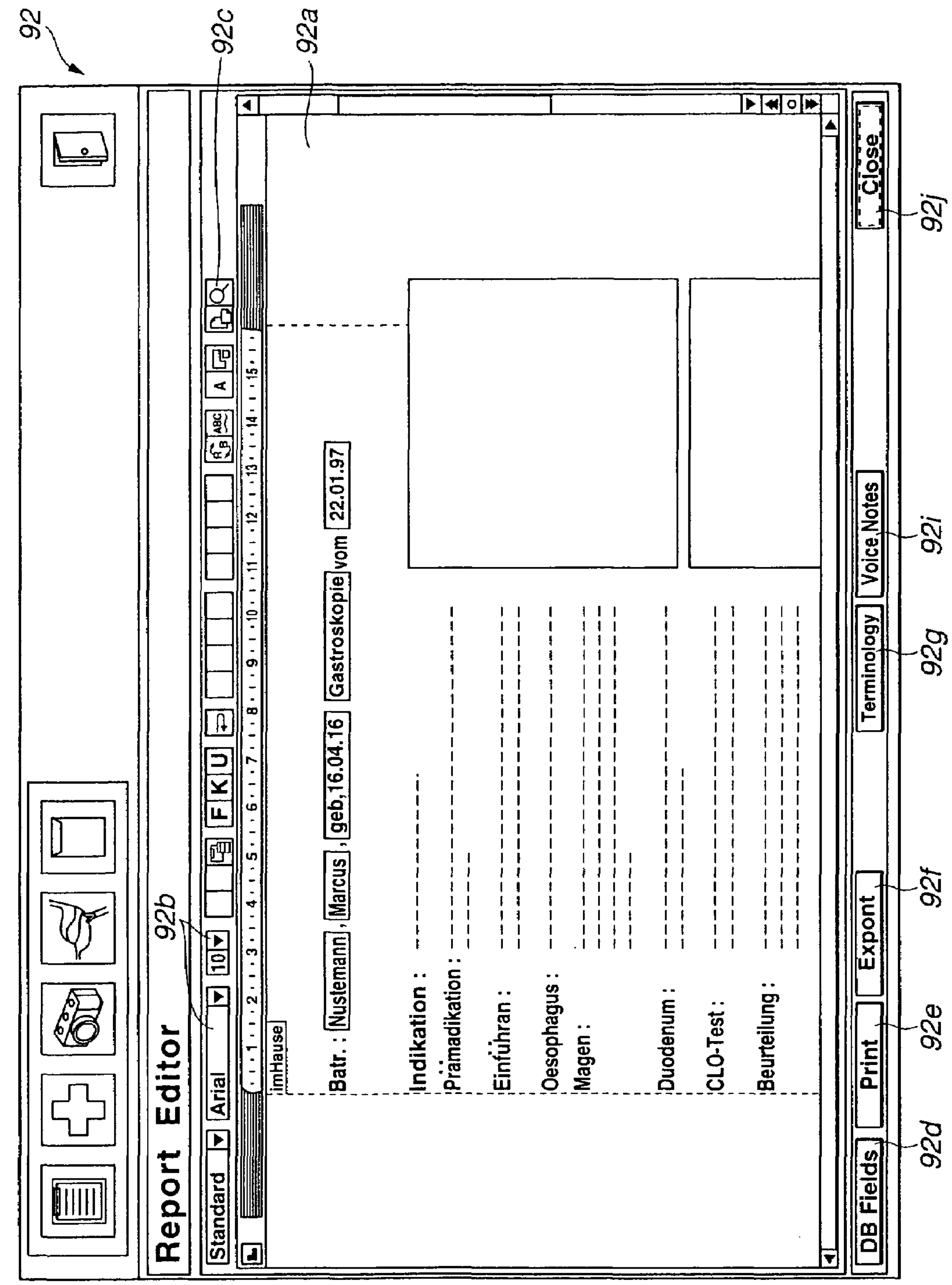
FIG. 14 shows an example of a screen display of an examination report editing screen.

FIGS. 13 and 14 are examples of the screen displays of the examination report creation screen 91 and the examination report editing screen 92, respectively, that are used to create and edit examination reports respectively. Clicking on a button 41*ge* of the schedule list screen 41 calls first the examination report creation screen 91 in FIG. 13.

Disposed in the examination report creation screen 91 as shown in FIG. 13 are: an image display area 91*a* for displaying thumbnail images of a plurality of images selected in the image selection screen 81; and an opinion structured entry area 91*b* for inputting an opinion.

The user enters an opinion in the opinion structured entry area 91*b* while referring to endoscope images displayed in the image display area 91*a*.

Disposed in the opinion structured entry area 91*b* is an internal site list display area 91*c* that displays the name of an internal site to which an attention is to be paid. The user is able to select a name for the internal site or similar to which an attention is to be paid, in the internal site list display area 91*c*.

Further, internal sites or similar of greater detail are sometimes contained in the selected internal site in the internal site list display area 91*c*.

An internal site list display area 91*d* for displaying the names of corresponding internal sites or similar of greater detail is therefore disposed in the examination report creation screen 91. The user is then able to choose a name for the internal site to which an attention is to be paid from this internal site list display area 91*d*.

Disposed below the internal site list display area 91*d* in the examination report creation screen 91 are: an attribute list display area 91*e* for displaying attributes as a list; and an attribute value list area 91*f* for displaying, as a list, the attribute values which correspond to the selected attribute, when a given attribute displayed in the attribute list display area 91*e* is selected.

When an attribute of interest is selected in the attribute list display area 91*e*, a choice of attribute values that correspond to the selected attribute is displayed in the attribute value list area 91*f*, which permits the selection of an attribute value. When, for example, the user selects "color" from among the attributes displayed in the attribute list display area 91*e*, red, blue, black, and so forth, are displayed for example as attribute values in the attribute value list area 91*f*.

Accordingly, the examination report creation screen 91 is constituted such that an opinion for these attributes and attribute values can be inputted in structured fashion by selecting an attribute and an attribute value relating to the internal site selected in the internal site list display areas 91*c* and 91*d*.

Accordingly, upon clicking on an Add button 91*g* of the examination report creation screen 91, opinion text is added to an opinion text list display area 91*h*, this opinion text being generated automatically from the subject word and predicate obtained via selections in the internal site list display areas 91*c* and 91*d*, the attribute list display area 91*e*, and the attribute value list display area 91*f*.

Furthermore, the examination report creation screen 91 is constituted such that selected opinion text can be deleted by selecting opinion text in the opinion text list display area 91*h* and clicking a Delete button 91*i*.

Disposed at the bottom of the examination report creation screen 91 are: a button 91*q* for switching the screen to the examination report editing screen 92; and a Close button 91*s* for closing the report creation screen and returning to the schedule list screen 41; a template selection field 91*t* for selecting a template to be used in the examination report editing screen 92; and a distribution destination setting button 91*u* for displaying the distribution destination setting screen 62, and so forth. When the buttons 91*q* to 91*u*, and the like, are clicked, the corresponding processing is executed.

Further, the distribution destination setting button 91*u* is constituted such that the number of distribution destinations set is displayed by a number in brackets in the button name display field.

The templates include: data indicating the layout of an examination report being created; data indicating the portion to be inserted in an examination report of examination data inputted in the search data editing screen 61 or similar; distribution data of report distribution destination data; data indicating the portion to be inserted in an examination report of endoscope images selected via the image selection screen 81; data indicating the portion to be inserted in an examination report of opinion text created in the examination report creation screen 91; and data indicating the portion to be inserted in an examination report of other data possessed by the image filing device 3.

A description will be provided next for the examination report editing screen 92 shown in FIG. 14.

Clicking on the button 91*g* of the examination report creation screen 91 of FIG. 13 described above switches the screen to the examination report editing screen 92 shown in FIG. 14.

The examination report editing screen 92 as shown in FIG. 14 has a report editing area 92*a* disposed therein. The report editing area 92*a* is constituted such that an examination report is displayed. The examination report has the following which are provided automatically in accordance with data included in the templates: examination data and endoscope images possessed by the image filing device 3, and opinion text and so forth created in the examination report creation screen 91.

In the same way as a publicly known word processor, document Add, Delete, Edit and Copy operations, and so forth, can be performed in the report image selection area 92*a*. Also like a publicly known word processor, the examination report editing screen 92 is provided with font selection fields 92*b* for setting the type and size, and so forth, of the text font used; and buttons 92*c* of a plurality of functions for calling various functions for editing text, such as a commonly known text formatting function, and a publicly known spell check function, and so forth, for example. The examination report editing screen 92 also makes it possible to shift the positions of images attached to an examination report, and to enlarge or reduce such images.

Disposed at the bottom of the examination report editing screen 92 are: an examination confirmation button 92*e* for calling the examination report output screen 93 for outputting an examination report; a Save button 92*f* for saving a text file of an examination report to a storage device such as the hard disk 21*e* and to an external storage device (not shown) in HTML format or similar, for example; a button 92*g* for switching the screen to the examination report creation screen 91; and a Close button 91*j* which, when clicked, closes the report creation screen to return to the schedule list screen 41. When the buttons 92*f* to 92*j*, and the like, are clicked, the corresponding processing is executed.

A description will be provided next for the examination report output screen 93.

Figure 15:
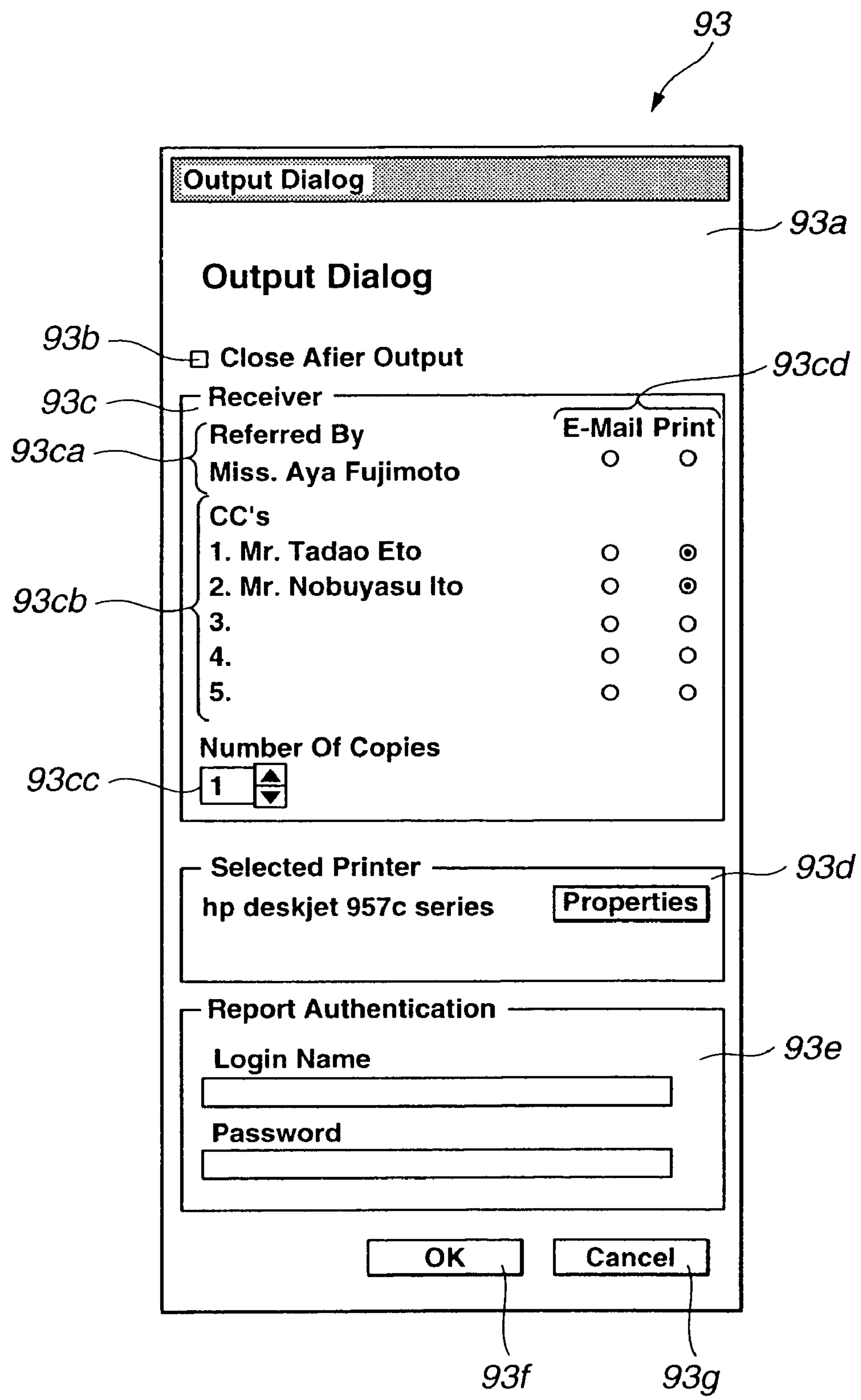
FIG. 15 shows an example of a screen display of an examination report outputting screen.

Clicking on the examination confirmation button 92*e* in the examination report editing screen 92 in FIG. 14 described earlier switches the screen to the examination report output screen 93 shown in FIG. 15.

FIG. 15 is an example of a screen display of the examination report output screen 93.

The examination report output screen 93 as shown in FIG. 15 is a screen for confirming the output method for the examination report and for registering an examination report history.

Disposed in the examination report output screen 93 is a check box 93*b* for electing to return to the examination report editing screen 92 or to the schedule list screen 41 after outputting is complete.

Also disposed in the examination report output screen 93 is an output method area 93*c* for setting the method to be used for an output to the examination report distribution destination. Disposed in this output method area 93*c* are: a referring party display field 93*ca* for displaying the referring party; and a distribution destination data display field 93*cb* for displaying distribution destination data set via the distribution destination setting screen 62 for the referring party displayed in the referring party display field 93*ca*. Disposed alongside the referring party display field 93*ca* and the distribution destination data display field 93*cb* is an output confirmation display field 93_cd_ for outputting the examination report by electronic mail or by making a printout.

The referring party display field 93_ca_, distribution destination data display field 93_cb_, and output confirmation display field 93_cd_ are displayed in accordance with the initial settings set in the institution distribution destination setting screen 102 and the individual distribution destination setting screen 103. The referring party display field 93_ca_, distribution destination data display field 93_cb_, and output confirmation display field 93_cd_ can also be modified via the examination report output screen 93.

A print number setting field 93_cc_ can also be displayed automatically and manually changed according to the print numbers set in the referring party display field 93_ca_ and the distribution destination data display field 93_cb_.

Disposed in the examination report output screen 93 is a button 93_d_ which, when clicked, displays a printer screen.

Further disposed in the examination report output screen 93 is an input area 93_e_ for inputting confirmation data serving to confirm the person responsible for outputting the examination report, such as user data and a password, for example. The examination report output screen 93 is constituted such that, in the absence of an input of confirmation data to the input area 93_e_, an examination report cannot be outputted.

Further, an outputted examination report can be referenced after processing a data handling history along with data on the person responsible for outputting the contents of the report.

The examination report output screen 93 also makes it possible to create a new examination report on the basis of examination reports that have already undergone the data handling history processing.

Disposed at the bottom of the examination report output screen 93 are: a Finish button 93_f_ for outputting an examination report in accordance with the output method displayed in the output method area 93_c_; and a Cancel button 93_g_ for closing the examination report output screen 93 to return to the examination report editing screen 92 without making an examination report output. When the buttons 93_c_ to 93_g_, and the like, are clicked, the corresponding processing is executed.

Figure 16:
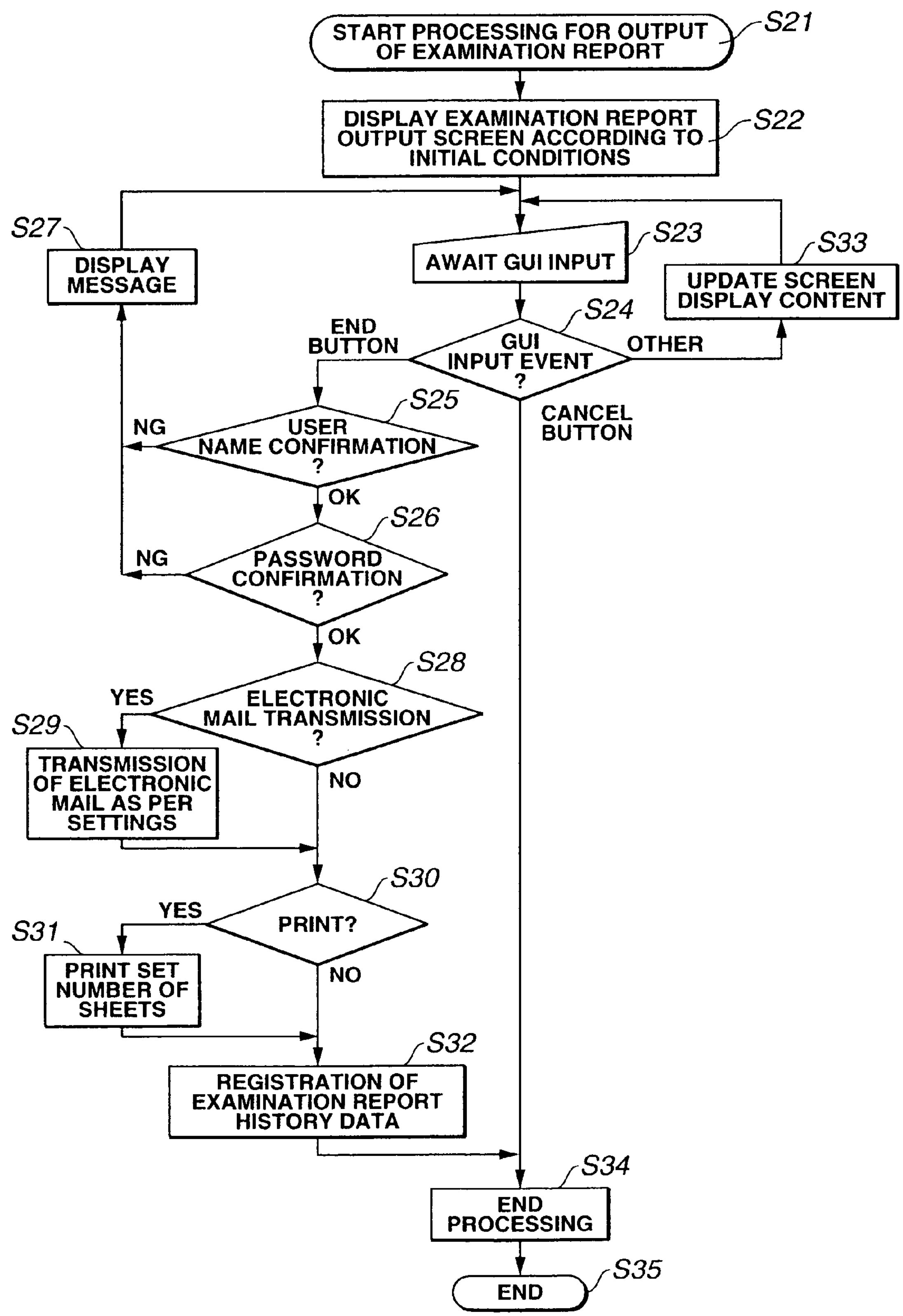
FIG. 16 is a flowchart illustrating the flow of processing for an output of an examination report.

Next, using the flowchart shown in FIG. 16, the flow of the execution of processing for an output of an examination report will be described. The reference numerals S21 to S35 in the figure are reference numerals assigned to processing steps. Further, these processing steps are performed through control performed by the CPU 21_a_ of the image filing device 3 on the basis of operation by the user, similarly to that described in FIG. 4.

The user creates an examination report by carrying out the processing steps S1 to S7 in the flowchart of FIG. 4 via the above-described display screens of FIGS. 5 to 14. The examination report output screen 93 is called by clicking on the examination confirmation button 92_e_ of the examination report editing screen 92 in FIG. 14.

Accordingly, the CPU 21_a_ of the image filing device 3 starts the display of the examination report output screen 93, which is displayed on the display screen of the monitor 22 (step S21).

Upon starting the display of the examination report output screen 93, the CPU 21_a_ searches for output distribution destination data pertaining to the examination report and displays the corresponding output method in the output method area 93_c_ in the examination report output screen 93 (step S22).

The CPU 21_a_ then sets the buttons 93_c_ to 93_g_ of the examination report output screen 93 to a GUI (Graphical User Interface) input wait state (step S23).

As a result of a button input (GUI input event) taking place in accordance with an input by the user via the mouse 24 or similar in step S23, the CPU 21_a_ confirms whether the input pertains to the Finish button 93_f_ or the Cancel button 93_g_ (step S24).

In step S24, even if neither the Finish button 93_f_ input nor the Cancel button 93_g_ input has been made, the CPU 21_a_ updates the displayed content of the examination report output screen 93 in accordance with the processing for the inputted button and returns the processing to step S23 (step S33).

On the other hand, when the Cancel button 93_g_ is inputted in step S24, the CPU 21_a_ performs end processing (step S34) and ends the execution of the examination report output processing, that is, closes the examination report output screen 93 (step S35).

When an input for the Finish button 93_f_ has been made in step S24, the CPU 21_a_ captures data on the person responsible for outputting that is inputted to the input area 93_e_ of the examination report output screen 93, and confirms whether this data is a user name managed in the system (step S25).

When, in step S25, the output handling person data is not a user name managed in the system, the CPU 21_a_ displays a message notifying this fact (step S27) and returns the processing to step S23.

On the other hand, when, in step S25, the output handling person data is a user name managed in the system, the CPU 21_a_ confirms whether or not the output handling person data involves a correct input of a password corresponding to the user (step S26).

When, in step S26, the output handling person data does not involve a correct input of a password corresponding to the user name, the CPU 21_a_ displays a message notifying this fact (step S27) and returns processing to step S23.

On the other hand, when, in step S26, the output handling person data involves a correct input of a password corresponding to the user name, the CPU 21_a_ confirms whether or not there is a specification to output the examination report by electronic mail (step S28).

When, in step S28, an output of the examination report is to be made by electronic mail, the CPU 21_a_ transmits an examination report electronic mail to the corresponding transmission destination(s) from the network I/F 21_m_ via the external network 26 in HTML format or another format (step S29). This electronic mail transmission may involve the encryption of the examination report using commonly known encryption technology.

Next, in step S30, the CPU 21_a_ confirms whether or not there is a specification to output the examination report via a printout. When, in step S30, there is a specification to output the examination report via a printout, the CPU 21_a_ prints out the designated number of copies of the examination report in accordance with the data on the corresponding transmission destination(s) (step S31).

Subsequently, the CPU 21_a_ records the examination report in examination report history data along with data on the party responsible for outputting the examination report (step S32), carries out end processing (step S34), and ends execution of the examination report output processing, that is, closes the examination report output screen 93 (step S35).

The endoscope image filing system 1 of the present embodiment is thus capable of automatically transmitting the details of an examination report to (a) designated distribution destination(s). The endoscope image filing system 1 of the present embodiment therefore permits an examination report to be confirmed instantaneously even in a location outside the system such as a remote location where a terminal is not installed, which enhances the convenience of use.

According to the present invention, it is clear that different embodiments are conceivable within a wide scope, based on the present invention and without departing from the spirit and scope of the invention. Other than being limited by the attached claims, the present invention is not limited to or by these specific embodiments.

What is claimed is:

1. An endoscope image filing system, comprising:

endoscope examined data inputting means for inputting endoscope examined data;

endoscope examined data recording means for recording endoscope examined data inputted by the endoscope examined data inputting means;

distribution destination data inputting means capable of designating and inputting a distribution destination outside the system as the distribution destination for an examination report on an endoscope examination;

report distribution destination data recording means for recording report distribution destination data inputted by the distribution destination data inputting means;

examined image recording means for recording endoscope image data obtained by an endoscope apparatus by relating such data with the endoscope examined data;

examination report creating means for creating an examination report by reading out endoscope image data from the endoscope image recording means to generate an endoscope image and by combining the examined image and the endoscope examined data; and distribution destination designating/outputting means for outputting a report created by the examination report creating means by designating a distribution destination outside the system on the basis of the report distribution destination data recorded by the report distribution destination data recording means, the distribution destination designating/outputting means checks a user name and password against pre-registered data on the person responsible for outputting after having authenticated to view the endoscope image data and the endoscope examined data, such that, in the event that the user name or password does not match the data on the person responsible for outputting, the examination report is not outputted.

2. The endoscope image filing system according to claim 1, wherein the endoscope examined data inputting means and the distribution destination data inputting means are a keyboard or a mouse; the endoscope examined data recording means, the report distribution destination data recording means, and the endoscope image recording means are a hard disk; and the examination report creating means and the distribution destination designating/outputting means are a CPU, ROM, and RAM.

3. The endoscope image filing system according to claim 1, wherein report distribution selecting means for selecting at least one report distribution means from a plurality of report distribution means for distributing the examination report are provided.

4. The endoscope image filing system according to claim 1, comprising:

report distribution destination advance registration means for registering the report distribution destination data in advance, wherein one or more report distribution destination data recorded by the report distribution destination data recording means is(are) selected from the report distribution destination advance registration means.

5. The endoscope image filing system according to claim 1, wherein examination report attached image selecting means for selecting an image to be attached to the examination report from the examined images recorded by the examined image recording means are provided.

6. The endoscope image filing system according to claim 1, comprising:

endoscope image data inputting means for inputting the endoscope image data from the endoscope apparatus, wherein the endoscope image recording means obtains the endoscope image data via the endoscope image data inputting means, based on a release trigger of the endoscope apparatus.

7. The endoscope image filing system according to claim 1, wherein the distribution destination designating/outputting means retrieve output distribution destination data which relates to the examination report and cause display means to display a corresponding output method; and assume a state of awaiting an input of a “Finish” or “Cancel” GUI (Graphical User Interface) or other GUI displayed by the display means, such that: when a “Finish” GUI is inputted, the distribution destination designating/outputting means check a user name and password against pre-registered data on the person responsible for outputting, transmit an electronic mail or perform printing in accordance with settings, record the examination report in history data along with data on the person responsible for outputting, and carry out end processing; when a GUI other than a “Finish” or “Cancel” GUI is inputted, the distribution destination designating/outputting means update the content of the screen display and return to the GUI input wait state; and when a “Cancel” GUI is inputted, the distribution destination designating/outputting means perform end processing.

8. The endoscope image filing system according to claim 3, wherein the report distribution means use electronic mail.

9. The endoscope image filing system according to claim 3, wherein the report distribution selecting means are a keyboard or a mouse.

10. The endoscope image filing system according to claim 4, wherein the report distribution destination advance registration means is a hard disk.

11. The endoscope image filing system according to claim 1, wherein, in the event that the user name or password is at variance with the pre-registered data on the person responsible for outputting, the distribution destination designating/outputting means cause display means to display a message to that effect, and then return to a GUI input wait state.

12. An endoscope image filing method, comprising:

an endoscope examined data inputting step of inputting endoscope examined data;

an endoscope examined data recording step of recording endoscope examined data inputted in the endoscope examined data inputting step;

a distribution destination data inputting step capable of designating and inputting a distribution destination outside the system as the distribution destination of an examination report on an endoscope examination;

a report distribution destination data recording step of recording report distribution destination data inputted in the distribution destination data inputting step;

an examined image recording step of recording endoscope image data obtained by an endoscope apparatus by relating such data with the endoscope examined data;

an examination report creating step of creating an examination report by reading out endoscope image data after the endoscope image recording step to generate an endoscope image and by combining the examined image and the endoscope examined data; and a distribution destination designating/outputting step of outputting a report created in the examination report creating step by designating a distribution destination outside the system on the basis of the report distribution destination data recorded in the report distribution destination data recording step, the distribution destination designating/outputting step checks a user name and password against pre-registered data on the person responsible for outputting after having authenticated to view the endoscope image data and the endoscope examined data, such that in the event that the user name and password do not match the data on the person responsible for outputting, the examination report is not outputted.

13. The endoscope image filing method according to claim 12, wherein a report distribution selecting step of selecting at least one report distribution step from a plurality of report distribution steps for distributing the examination report is provided.

14. The endoscope image filing method according to claim 12, comprising:

a report distribution destination advance registration step of registering the report distribution destination data in advance, wherein one or more report distribution destination data recorded in the report distribution destination data recording step is(are) selected after the report distribution destination advance registration step.

15. The endoscope image filing method according to claim 12, wherein an examination report attached image selecting step of selecting an image to be attached to the examination report from the examined images recorded in the examined image recording step is provided.

16. The endoscope image filing method according to claim 12, comprising:

an endoscope image data inputting step for inputting the endoscope image data from the endoscope apparatus, wherein, the endoscope image recording step obtains the endoscope image data after the endoscope image data inputting step, based on a release trigger of the endoscope apparatus.

17. The endoscope image filing method according to claim 12, wherein the distribution destination designating/outputting step retrieves output distribution destination data which relates to the examination report and causes a display step to display a corresponding output method; and assumes a state of awaiting an input of a "Finish" or "Cancel" GUI (Graphical User Interface) or other GUI displayed in the display step, such that: when a "Finish" GUI is inputted, the distribution destination designating/outputting step checks the user name and password against the pre-registered data on the person responsible for outputting, and transmits an electronic mail or performs printing in accordance with settings, records the examination report in history data along with data on the person responsible for outputting, and carries out end processing; when a GUI other than a "Finish" or "Cancel" GUI is inputted, the distribution destination designating/outputting step updates the content of the screen display and returns to the GUI input wait state; and when a "Cancel" GUI is inputted, the distribution destination designating/outputting step performs end processing.

18. The endoscope image filing method according to claim 13, wherein the report distribution step uses electronic mail.

19. The endoscope image filing method according to claim 12, wherein, in the event that the user name or password is at variance with the pre-registered data on the person responsible for outputting, the distribution destination designating/outputting step causes a display step to display a message to that effect, and then returns to a GUI input wait state.

* * * * *